United States Patent [19]

Sitte et al.

[11] Patent Number: 5,070,935

[45] Date of Patent: Dec. 10, 1991

[54] REFRIGERATED CHAMBER FOR OBTAINING THIN SLICES AT LOW TEMPERATURE

[76] Inventors: Hellmuth Sitte, Reitherspitzstrasse 166, A-6100 Seefeld, Austria; Helmut Hässig, Am Gedünner 21, D-6650 Homburg-Saar; Klaus Neumann, Eichenstrasse 8, D-6652 Bexbach-Saar, both of Fed. Rep. of Germany

[21] Appl. No.: 348,622

[22] PCT Filed: Oct. 13, 1987

[86] PCT No.: PCT/EP87/00596

§ 371 Date: Apr. 14, 1989

§ 102(e) Date: Apr. 14, 1989

[87] PCT Pub. No.: WO88/02851

PCT Pub. Date: Apr. 21, 1988

[30] Foreign Application Priority Data

Oct. 14, 1986 [AT] Austria ................................. 273/86

[51] Int. Cl.⁵ ............................ F25C 5/02; F25B 29/00
[52] U.S. Cl. ........................................ 165/61; 62/49.2; 62/320; 83/915.5
[58] Field of Search ................... 62/320, 49.2; 83/170, 83/171, 915.5; 165/30, 61; 250/443.1

[56] References Cited

U.S. PATENT DOCUMENTS 4,284,894 8/1981 Sitte et al. .................... 250/443.1
4,489,569 12/1984 Sitte ............................... 62/49.2

FOREIGN PATENT DOCUMENTS 2246853 9/1972 Fed. Rep. of Germany .
2328298 3/1974 Fed. Rep. of Germany .
1170796 11/1969 United Kingdom .

Primary Examiner—William E. Wayner
Attorney, Agent, or Firm—Wenderoth, Lind & Ponack

[57] ABSTRACT

A refrigerated chamber includes, inside a metal wall and a foam insulating layer thereof, a sheet metal tank, in which, depending on levels of filling with liquid nitrogen, various compartments of the tank divided by separations, of different height are filled with $LN_2$. Thereby, different cooling powers are available for varying temperature ranges between ambient temperature and the temperature of the liquid nitrogen. In this way one avoids an excessive consumption of nitrogen. Filling with $LN_2$ is effected from a separating tank by means of a horizontal small-diameter pipe which during operation of the chamber is always exposed to and cooled by liquid nitrogen. Nitrogen in the form of a sweeping gas emerges in a boiling state from the tank and is guided through a cutting space (41') and can be heated by a heating plate fixed to sheet metal deflectors.

28 Claims, 19 Drawing Sheets

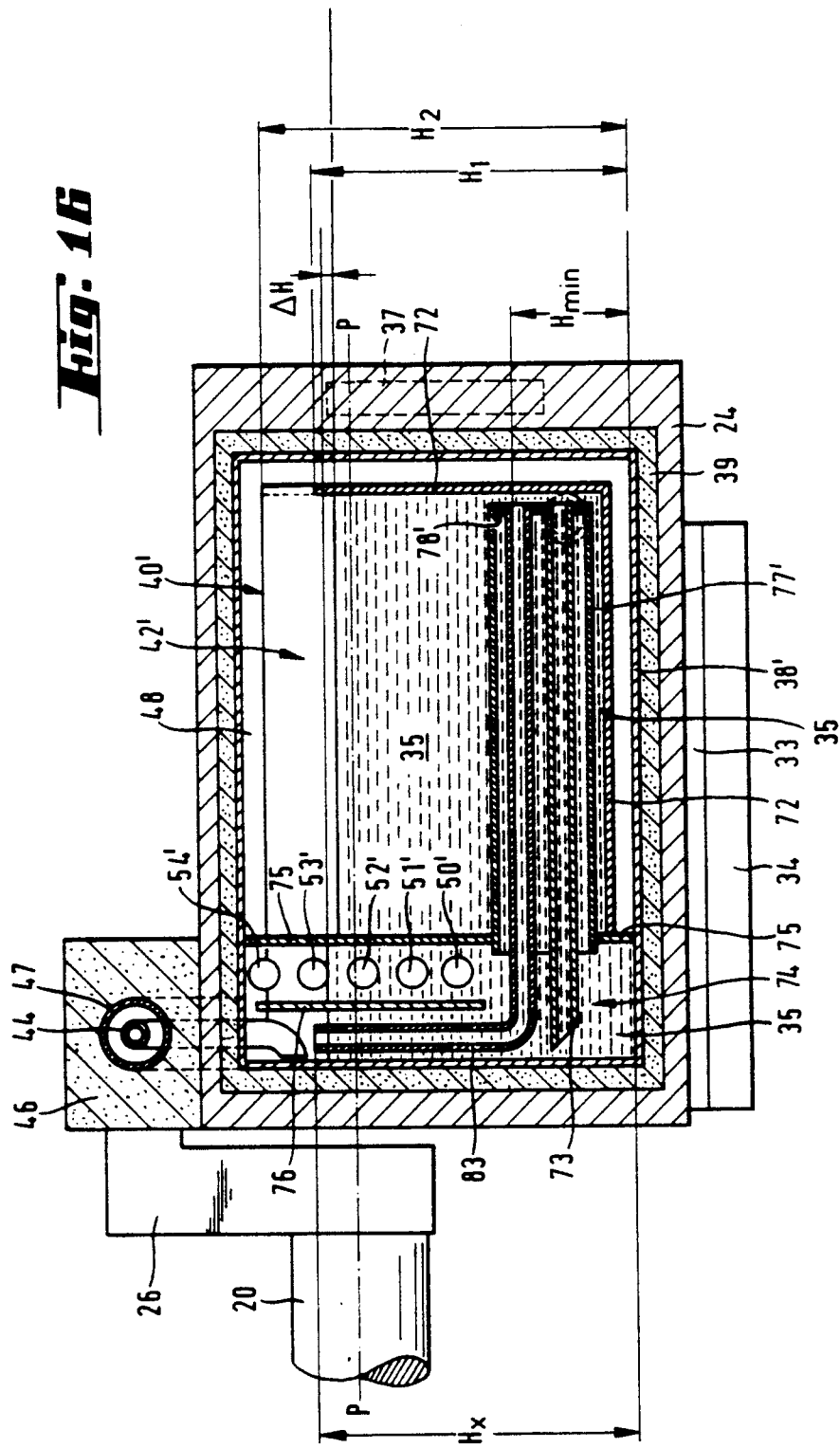

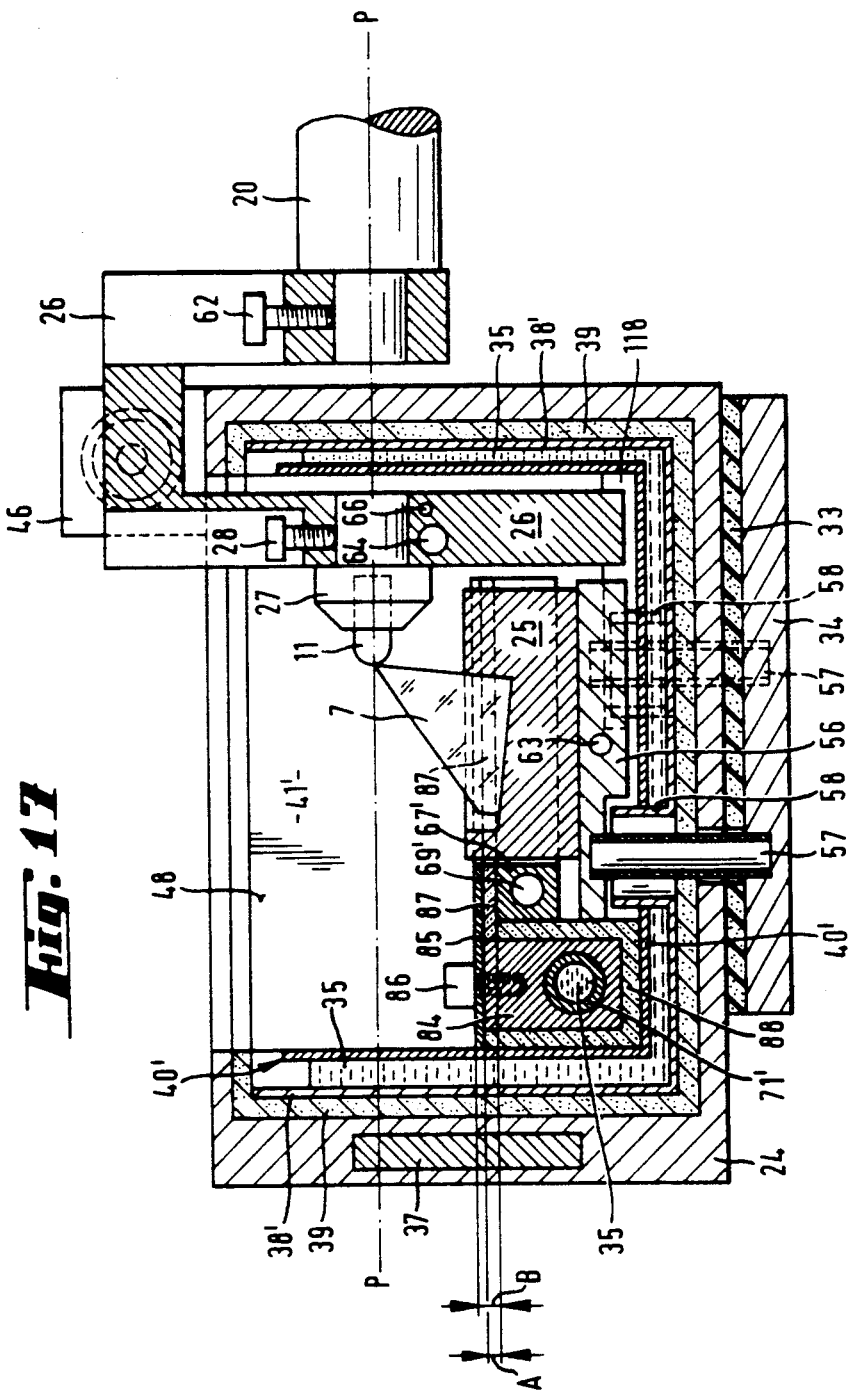

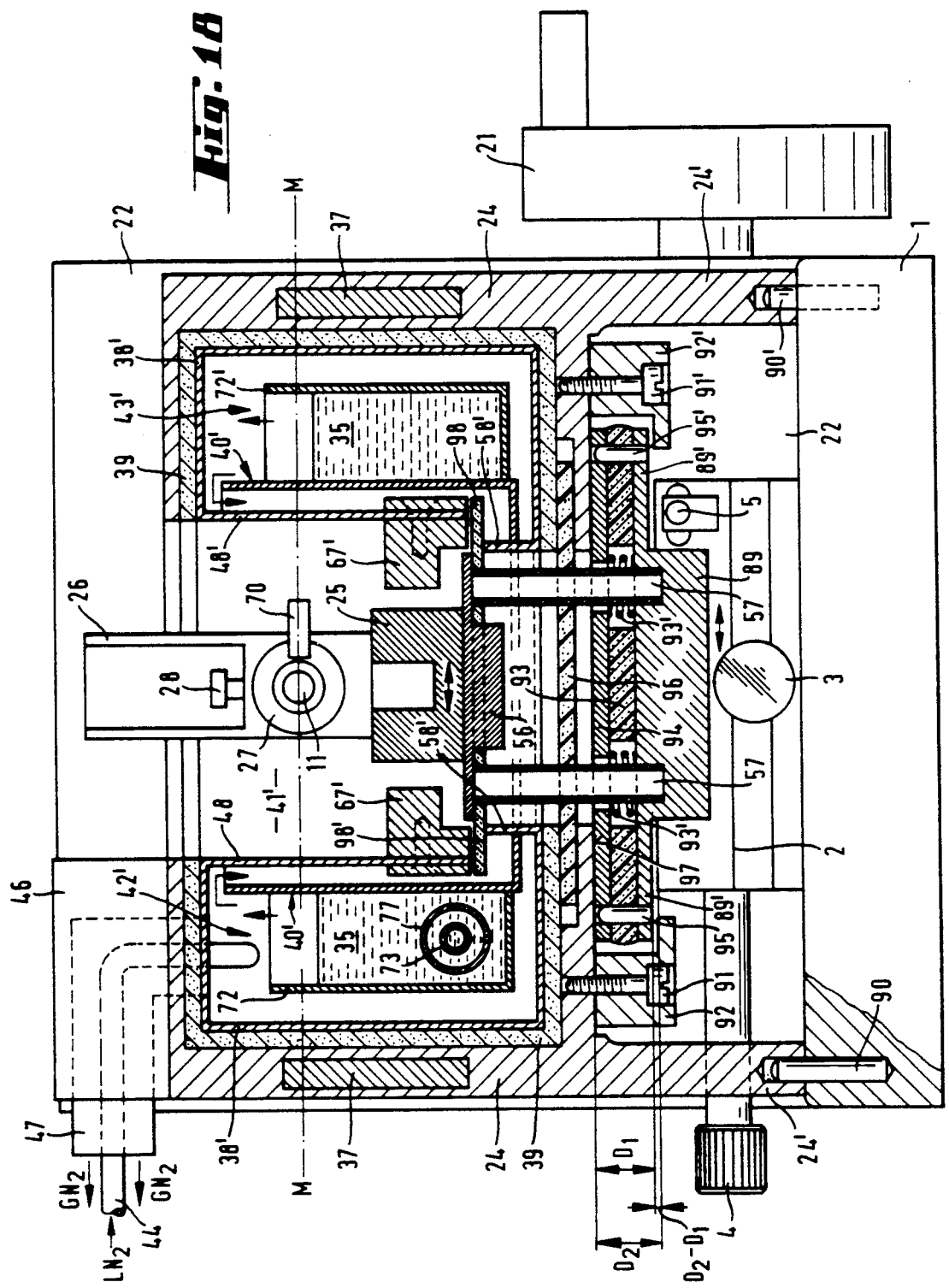

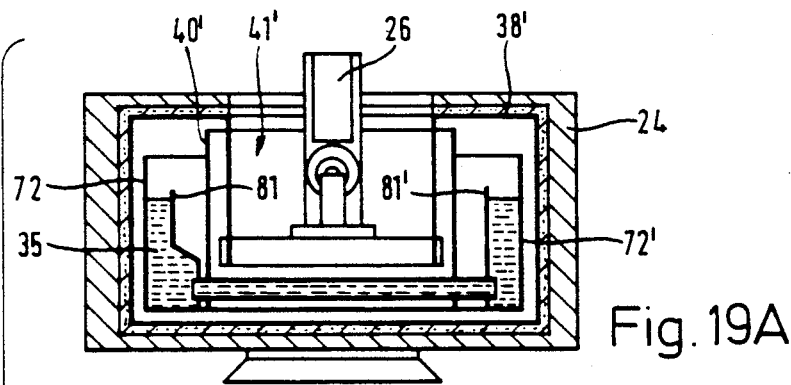
Fig. 19A
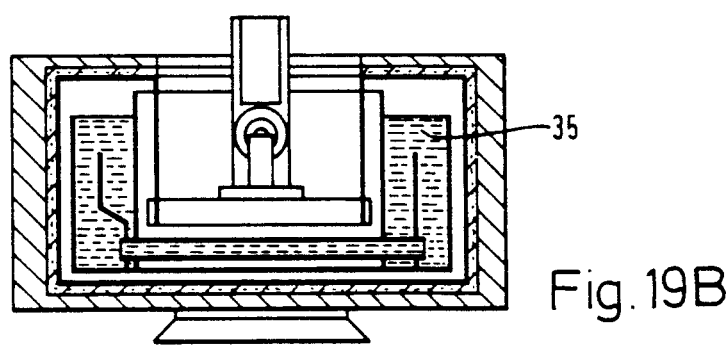
Fig. 19B
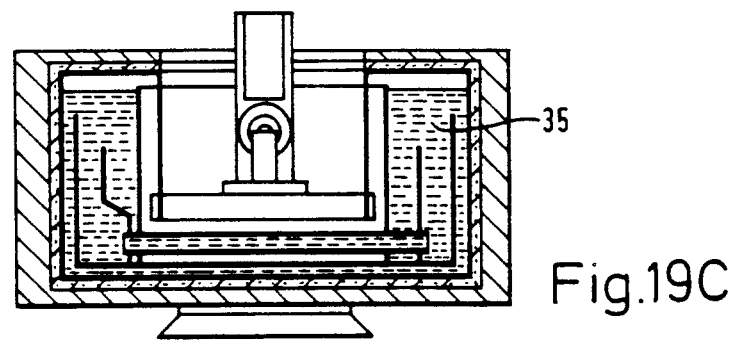
Fig. 19C
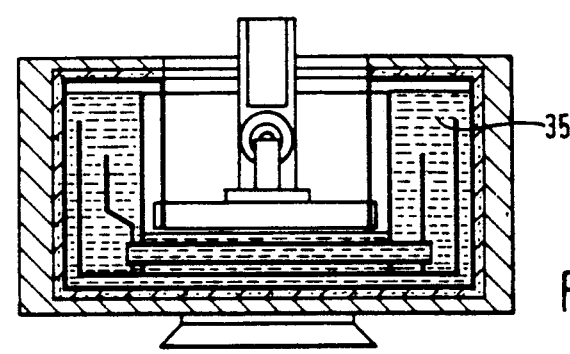
Fig. 19D
Fig. 19

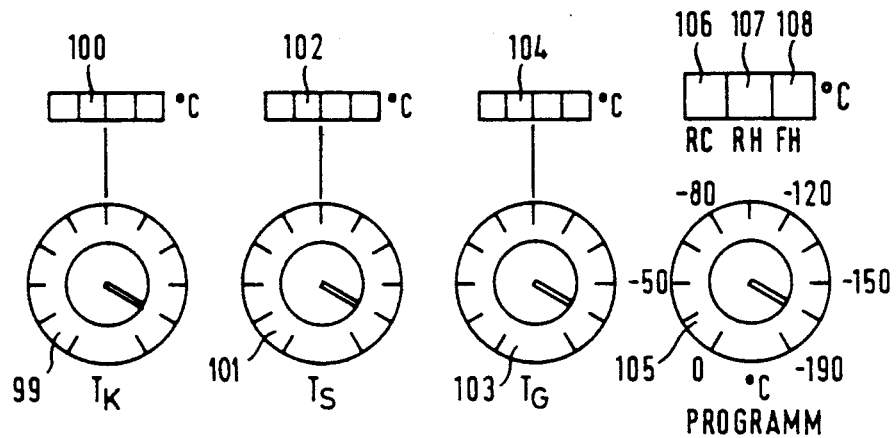
Fig. 20
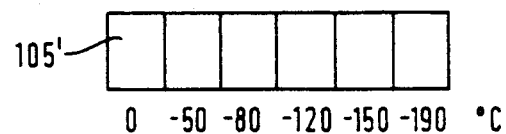
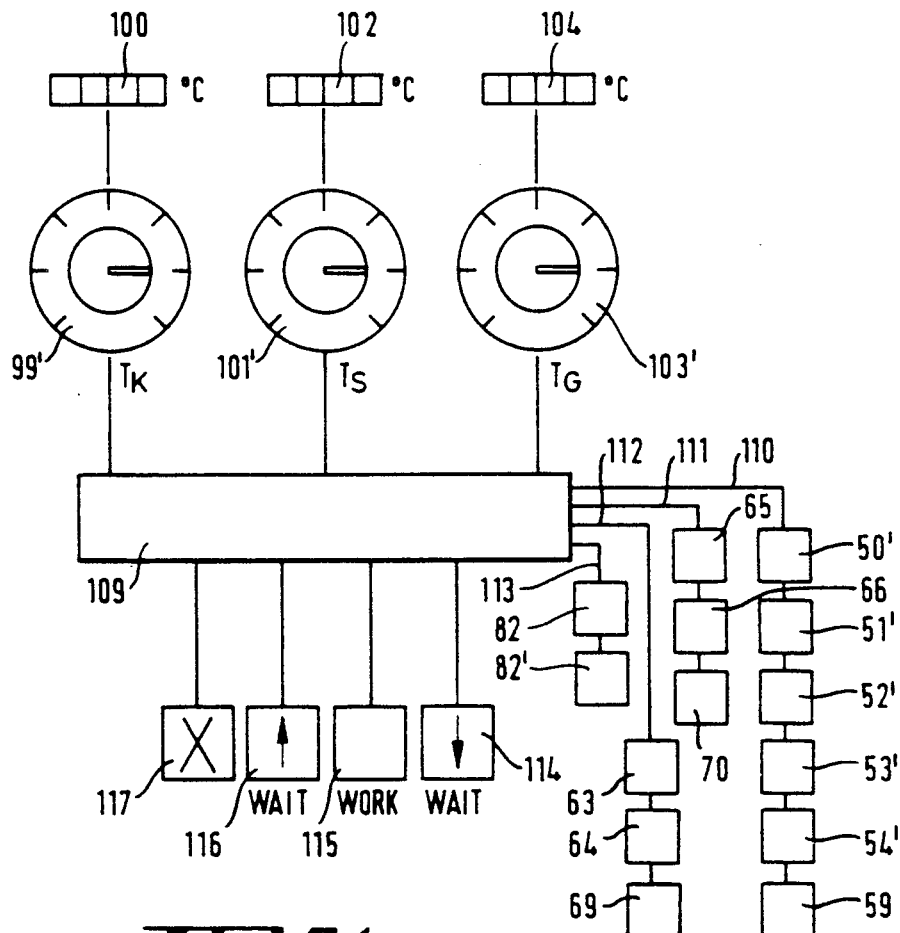
Fig. 21

REFRIGERATED CHAMBER FOR OBTAINING THIN SLICES AT LOW TEMPERATURE

BACKGROUND OF THE INVENTION

The invention relates to a cooling chamber cooled by liquid nitrogen ($LN_2$) and swept with gaseous nitrogen ($GN_2$) and intended for producing thin, particularly ultra-thin, sections for microscopic and electron microscopic examination.

According to the current state of the art, $LN_2$ cooled and $GN_2$ swept or $GN_2$ filled cooling chambers are preferably used in the field of cryo-ultramicrotomy for electron microscope examination of viscoplastic antiadhesive or biomedical objects, instead of the previously used cooling cartridges or cryostat systems (cf. H. SITTE, Instrumentation for Cryosectioning, in: "Electron Microscopy 1982, Vol. 1, 10th Int. Congress on Electron Microscopy, Hamburg, pp. 9 to 18; H. SITTE and K. NEUMANN, Ultramicrotomes and appliances for ultramicrotomy, Geratetechnik—Funktion—Zubehor, in: G. SCHIMMEL and W. VOGELL: A collection of methods for electron microscopy, contribution 1.1.2, Wiss. Verl. GmbH, Stuttgart 11, 1984, 1 to 248, particularly pp. 69 to 91; C. REICHERT AG, A-1170Vienna. Catalogue 1.K.-FC 4 D-D 4/84, FC 4 D Low Temperature Cutting System according to SITTE, 1984; C. REICHERT AG, A-1170 Vienna, Catalogue 1.K.-CRYO PREP. E-8/86, Cry preparation for superior EM investigation, 1986). With the currently preferred FC 4 D system of REICHERT AG in A-1170 Vienna, a cutting space in which a frozen object and a knife are located is an open topped sheet aluminum box which is directly cooled by $LN_2$. For this purpose, having regard to the available space with an ultramicrotome, there are on the right and left two intercommunicating sheet aluminum tanks ("a twin tank system") to accommodate about 1 liter of $LN_2$ and these are connected to the cutting chamber. This arrangement (twin tanks with cutting chamber) makes it possible to achieve minimal temperatures which come very close to the boiling point of $LN_2$ ($-196°$ C.), and also make it possible to work with an open cutting room ("open top work") without the risk of ice deposits in the object knife area. This situation owes much to a strong $GN_2$ current which is constantly being vaporized from the $LN_2$ which is used as the cryogenic medium and which is partially deflected by baffle plates to the bottom of the cutting chamber. In this way, the cutting chamber is swept from the bottom upwards by a stream of cold, dry $GN_2$ which on the one hand cools the object and the knife and also supports therefor, while on the other it prevents the ingress of humid room air into the cutting chamber. Since with regard to the heat and cold sensitivity of the ultramicrotome mechanism, it is also necessary to avoid frost deposits as well as cold surfaces on the outside of the tank system, the system described is enclosed by an insulating layer of foamed synthetic plastic (e.g. foamed polystyrene or polyurethane) and finally a chamber wall which is thermostatically heated to room temperature and which consists of a readily heat conductive material (e.g. cast aluminum) (see inter alia H. SITTE, K. NEUMANN, H. KLEBER and H. HASSIG, Cooling Chamber for Holding Objects Requiring Work, Particularly Biological Objects, German Patent Application No. 29 06 153 C 2 of Feb. 17, 1979). Such a chamber wall not only prevents frost forming, which cannot be avoided after prolonged use even with a relatively thick layer of insulation, but at the same time it warms the $GN_2$ flowing over the outside walls up to temperature levels which no longer have a disturbing influence on the sensitive ultramicrotome mechanism. The chamber wall is, via a resilient interlining, fixed on an assembly element (e.g. a dovetail joint), by means of which it can be mounted on the knife support of the microtome or ultramicrotome. The assembly element carries a baseplate for the cutter holder in a rigid metallic connection. In contrast, the object is now generally fixed on a bridgelike carrier element which is mounted on a preparation carrying arm of the microtome or ultramicrotome and plunges down into the cutting chamber from above (CHRISTENSEN'S "bridge", see A. K. CHRISTENSEN, J. Cell Biol. 51, 1971: 772–804). Where such cooling chambers are concerned, vital importance is attached to the way in which the tank system is filled or topped-up with $LN_2$. As a rule, the $LN_2$ tank is filled through a pipe from a storage tank (e.g. 50 liter Dewar tank). Since a continuous $LN_2$ top-up is very difficult to achieve by reason of substantially varying working conditions, topping-up is intermittent and is controlled by measuring probes (e.g. thermosensitive diodes) so that topping-up with $LN_2$ starts when there is a preselected minimal level of $LN_2$ in the twin tanks and is stopped again when a likewise preselected maximum level is reached. After topping-up with $LN_2$ is stopped, there is a pause in which $GN_2$ is decocted from the $LN_2$ present in the tank system of the cooling chamber until such time as the minimal $LN_2$ level is again reached and another topping-up process commences. In the time elapsing between two topping-up processes, a hose connection between the Dewar storage tank and the cooling chamber becomes sufficiently heated so that for a fresh top-up with $LN_2$ it is necessary firstly to cool down again to $-196°$ C. This causes a violent boiling process during which large quantities of $GN_2$ are given off which in turn, as they pass through the cutting chamber, have a disturbing influence on the cutting process. Therefore, emergence through the cutting chamber of this $GN_2$ which is initially formed during the topping-up process is prevented by an $LN_2$ liquid barrier of the same type as a siphon normally used in a sanitary installation as a seal vis-a-vis a sewage system ("a phase separator" for separating the $GN_2$ from the $LN_2$ during topping up). Cooling chambers currently equipped with such "separators" react to the initial surge of $GN_2$ during topping-up but only in a very weakened manner.

Very soon it became obvious that the minimum attainable object and cutter temperature does not in most cases represent the optimum temperature for the taking of sections. For example, in order to take sections in thicknesses of between 0.5 and 1 $\mu$m from biomedical specimens which, prior to being frozen, have been treated with aldehyde and sugar solutions by the TOKUYASE method currently used for histochemistry (see G. GRIFFITH and coll., J. Ultrastructure Res. 89, 1984: 65 to 78), a temperature around $-80°$ is optimum, since at lower temperatures, the frozen material becomes too brittle and crumbly for taking sections of this thickness. If one would like to take from the same specimen, for electron microscopic investigation, ultrathin sections in thicknesses $\leq 0.1$ $\mu$m, then this is possible only by reducing the temperature to about $-100°$ C. If it is desired to cut biomedical specimens which become amorphously vitrified by rapid cryofixation, in this amorphous state, then these section preparations must be carried out in a temperature range below −140° C., since amorphously vitrified water changes to cubic-crystalline water at the devitrification temperature of −135° C., so that the sensitive fine structures are destroyed. Finally, many visco-plastic and/or antiadhesive polymers (e.g. natural or synthetic rubber, TEFLON, polyethylenes) can only be cut at below their glass point, since it is only then that they attain the hard consistency needed for cutting. Many substances (e.g. silicone rubber, TEFLON) only attain this consistency in the immediate vicinity of the boiling point of $LN_2$, i.e. around −190° C.

Chambers of the described construction indeed reach ultra low temperatures without any problems, close to −190° C. and are therefore outstandingly suitable for cutting amorphously vitrified biomedical objects and for cutting polymers with an extremely low glass point. However, they are only conditionally suitable for cutting biomedical specimens after a sugar impregnation according to TOKUYASU's method in the temperature range $\geq -100°$ C. It has been demonstrated that indeed the metallic object and knife support can be very rapidly heated to values $\geq -100°$ C. by means of a heating cartridge but that by reason of the violent scavenging of the object and the knife by cold $GN_2$, the tip of the object and the edge of the knife nevertheless stay at temperatures which are far closer to the temperature of the cold scavenging gas (about −170° C. at the level of the knife edge) than to the temperatures of the heated metal supports. Therefore, with such systems, one is compelled likewise substantially to heat up the $GN_2$ scavenging gas. According to the current state of the art, this is carried out by a heated metal plate mounted in the bottom of the chamber and over which the cold stream of $GN_2$ is directed. Thus, it indeed is possible to achieve the desired heating of the scavenging gas from −170° to about −100° C. and, as the process continues, usable working conditions in the temperature range of up to about −80° C., but one does firstly fall foul of the limit of the potential of such systems while secondly the facility achievement is paid for by a considerable increase in $LN_2$ consumption. The intimated limit of possibility is a kind of "vicious circle", i.e. the heating elements in the chamber, particularly the heating plate mounted in the bottom of the chamber for heating the $GN_2$ scavenging gas, causes a more violent boiling off of $GN_2$ from the $LN_2$ tank, thus increasing cooling by the $GN_2$ scavenging gas and finally causing a more pronounced output of heat in the chamber. This working cycle limits the counter-heating to $GN_2$ temperatures of around −100° C. The $LN_2$ consumption of the system thereby increases from about 3.5 liters $LN_2$/hr for a cutting chamber of about 1 liter capacity without counter heating ($GN_2$ temperature −170° C.) to about 7 liters $LN_3$/hr with counter heating which produces a $GN_2$ temperature of around −100° C. in the same system. Since this increased $LN_2$ consumption is $\epsilon$ genously produced, i.e. by the heat output from the gas heating plate in the cutting chamber, it cannot be outwardly diminished by increasing the foam insulation around the tank system. Apart from this disturbing phenomenon which in addition renders impossible section preparations in the temperature range of between 0° and −50° C. which is normally used for conventional cryostat systems of light-microscopic histochemistry and micromorphology in such cooling chambers, the section preparation is affected by the initial release of $GN_2$ in the connecting tube between the Dewar storage tank and the chamber tank, despite the interposed separator systems, because these cannot prevent the wave motion of the $LN_2$ in the twin tank which is triggered by the shock waves. In consequence, the $LN_2$ in the twin tank briefly wets areas of the chamber walls of which the temperatures are somewhat above the boiling temperature. It necessarily follows that there is also an onset of boiling of the $LN_2$. The $GN_2$ which is liberated is deflected by baffle plates into the cutting chamber where it causes the temperature to drop by about 1° to 3° C. and as the process continues some of the microsections in the section strip may be unsuccessful. Finally, practice has shown that the assembly of heavy and all in all large-volume and extensive chambers (volume totalling over 4 liters, dimensions: height × width × depth about 15 × 25 × 15 cc) on a precision cross slide for the supporting of a microtome or ultramicrotome is not sufficiently stable. Rather, despite all manner of protective measures, in the virtually inevitable event during preparation of the sections that, a hand is placed on the chamber wall, there will be a tendency to allow a troublesome change in the relative position between the preparation and the knife which makes it virtually impossible immediately and without risk to continue a series of sections following such an interruption.

SUMMARY OF THE INVENTION

Therefore, the object of the invention is to eliminate the aforesaid disadvantages of the chamber construction described according to the state of the art, which means improving the chamber particularly in the way in which, at reduced temperatures over the total range between room temperature and −190° C., the preparation of sections is guaranteed without any substantial increase in $LN_2$ consumption by the system (for example, above about 3.5 l/hr) due to the counter-heating of the object and knife support, and of the $GN_2$ scavenging gas. According to the invention, this aim is achieved in that, in the tank system on opposite sides of the cutting chamber inside the $LN_2$ container there are two inserted tanks which are connected to each other by a separate $LN_2$ connection which is preferably close to the bottom, the mutually facing lateral wall surfaces of the two inserted tanks possibly being parts of the metal walls of the cutting chamber. At least one portion of the outer lateral or of the front or rear walls of at least one of the two inserted tanks in each case has a minimum height which is less than the minimum height of a portion of the vertical metal walls of the cutting chamber. The $GN_2$ from the tank system which is entirely deflected by metal baffle plates onto the bottom of the cutting chamber possibly (and if required) is heated by preferably a gas heating arrangement comprising a gas heating plate and fixed solely on the baffle plates, the gas heating arrangement in turn having no solid surface contact with the metal parts of the walls of the cutting chamber. The two inserted tanks are in this case so disposed inside the two $LN_2$ tanks of the "twin tank system", on opposite sides of the cutting chamber, that the $LN_2$ in the inserted tanks either does not wet the walls of the cutting chamber at all or alternatively the vertical side walls of the inserted tanks which face the cutting chamber represent a part of the vertical side wall of the respective twin tank while the other side walls and the bottoms of the two inserted tanks form separate wall elements. The inserted tanks are entirely open at their tops or at least have an apertures which, in the event of over-filling, allow $LN_2$ to overflow into the twin tank system, thus allowing afterwards a type of operation which corresponds to operation of the initially described chamber for low temperature preparations in the range between $-120°$ and $-190°$.

By improving the separator system, a further object of the invention is to permit uninterrupted production of cryomicrosections even during the onset of $LN_2$ addition. According to the invention, this is achieved in that for topping up the tank system there is integrated into the cooling chamber a separate separator tank with an $LN_2$ supply line and a $GN_2$ discharge line, from which the inserted tanks or the $LN_2$ containers are supplied with $LN_2$ through a substantially horizontally extending narrow-gauge separator tube which under normal working conditions is constantly flushed and cooled by $LN_2$. The separator chamber or tank is a separate compartment of the two $LN_2$ containers inside the twin tank system and which, in contrast to the state of the art wherein during normal working conditions of the cutting ready system is in the $GN_2$ zone, is completely isolated from the $GN_2$ zone of the other tank system (twin tank including inserted tanks). There exists in the $LN_2$ zone, during normal working conditions, between the $LN_2$ zone of the separator tank and the $LN_2$ zone of the other tank system and via one of the two inserted tanks, only a connection by a pipe of sufficient length (e.g. $\geq 80$ mm) which is constantly flushed by $LN_2$ and which is therefore constantly cooled to $LN_2$ boiling temperature, the pipe having a sufficiently small inside diameter (e.g. $\leq 4$ mm), through which $LN_2$ from the separator chamber is added to top up the rest of the tank system, the topping-up being electronically controlled by $LN_2$ level sensors (e.g. thermosensitive diodes or measuring resistors).

If they are not over-filled in the manner referred to, the effect of the inserted tanks is that the walls of the cutting chamber are either not wetted by $LN_2$ at all or that only a limited portion of the wall of the cutting chamber is directly cooled by $LN_2$, the surface area of this directly cooled wall surface possibly being additionally varied by controlling the level of the $LN_2$ contents. In contrast, $LN_2$ does not come in contact directly with the other outer surfaces of the tank system. $LN_2$ loss due to the inflow of heat which always takes place via the foam insulation from the heated chamber wall is therefore substantially reduced. To the same extent there is a reduction in the quantity of the currently boiled-off $GN_2$, so that the working cycle described between counter-heating and $GN_2$ scavenging gas formation is effectively interrupted. The separator tank has the effect of minimising the wave motion of the cryogen in the rest of the tank system so that it no longer interferes with the cutting process, in other words during the current series of sections there will be no failure of micro sections when topping-up with $LN_2$ starts. The gas heating arrangement which comprises, for instance, a gas heating plate and which is fixed solely on the deflector plates in turn, in contrast to the state of the art with the $LN_2$ tank system, no longer is in direct thermal contact with the walls of the cutting chamber over metallic intermediate members of minimal length, so that during operation it therefore influences only to a comparatively minor extent an increase in $LN_2$ consumption and thus an intensification of the flow of $GN_2$ scavenging gas.

A further development of the invention resides in that each of the two inserted tanks is sub-divided by a predominantly vertical partition installed therein preferably parallel with and symmetrical in relation to the plane of symmetry of the chamber, into two compartments, the outer compartment of which that is not directly adjacent the side wall of the cutting chamber being connected to the symmetrically corresponding compartment of the other inserted tank by the connecting tube. The height of the partitions is so chosen that the $LN_2$ from whichever is the outer compartment flows into the inner compartment which is towards the cutting chamber, before $LN_2$ overflows from the inserted tanks into the rest of the tank system. Thus, differentiation in the $LN_2$ filling of the tank system is achieved in such a way that initially $LN_2$ flows from the separator tank into one of the outer compartments and, via the connecting tube, fills whichever is the corresponding outer compartment of the other inserted tank. While this is happening, the walls of the cutting chamber are cooled only by the sheet metal connection between the wall portions and the bottom of the inner compartments of the two inserted tanks which are as yet not filled with $LN_2$. The effect of this cooling can be minimised if required by constructing the tank from rust-resistant stainless steel of minimal thickness and low heat conductive capacity or may be enhanced as required by the choice of sheet aluminum of greater thickness. It is likewise possible to achieve differentiation by selection of the width of the inner compartments. If the outer compartments are overfilled, then firstly the inner compartments of the two inserted tanks will be filled with $LN_2$ which thus for the first time, in the manner described, comes into contact with partial zones of the opposite side walls of the cutting chamber. The cooling effect is markedly enhanced thereby. Upon further filling of the tank system, the maximum cooling effect is achieved in that the total twin tank assembly is filled with $LN_2$. In an extreme case, in addition to the bottom, all the side walls of the cutting chamber will be directly cooled with $LN_2$. Control by level sensors limits the $LN_2$ filling and thus the $LN_2$ direct cooling to a certain height of $LN_2$ or to a certain area of cooling.

A further development of the invention resides in that there are, in the interiors of the undivided inserted tanks or in the outer compartments of inserted tanks which are divided into two compartments by suitable partitions, heating elements which lead to a controlled increase in the quantity of $GN_2$ boiled off, to thus produce a desired increase of an inadequate flow of $GN_2$ scavenging gas which would no longer ensure freedom of the cutting chamber from frost. Especially in the case of high chamber gas temperatures and/or extremely reduced $GN_2$ flow, this measure is necessary since if the $GN_2$ scavenging gas temperatures come close to room temperature, the difference in density between the scavenging gas and room atmosphere diminishes. Therefore, if the situation continues—particularly with a minimal throughput of $GN_2$ through the cutting chamber—low turbulence or flow in the air will lead to humid room air being brought into the cutting chamber with the danger of frost or condensate forming on the cold surfaces therein.

A further development of the invention resides in that the two inserted tanks are connected to the walls of the cutting chamber, apart from the walls of the separator tank, solely via the connecting tube which ensures discharge of $LN_2$ from one inserted tank into the other.

Since only very reduced heat transfer is possible via these contact points, a system which is thus simplified operates with minimal $LN_2$ consumption and represents a particularly simple way of permitting working temperatures to be around 0° C.

A further development resides in that for a higher level of $LN_2$ filling the cooling chamber, which as a rule is linked with higher $LN_2$ consumption due to increased heat exchange between the chamber wall and the outer walls of the twin tanks, a second angled separator tube results in additional discharge of $LN_2$ from the separator tank into one of the inserted tanks.

A further logical development resides in that there is fixed on the connecting tube between the two inserted tanks a highly heat-conductive metal profile member which is in turn connected to a likewise readily heat-conductive metal plate which covers the gas heating plate from which it is thermally separated, either by a gas filled intermediate space or by a heat insulation, so that a cold plate is available as a worktop or area for preparatory work in the cutting chamber.

A further development of the invention resides in that the cooling chamber is not mounted via its metal chamber wall on the cross slide of the microtome or ultramicrotome in the long since hitherto conventional manner, but is mounted on the microtome or ultramicrotome base itself, and that only the knife holder is rigidly connected to the cross slide, a sealing member preventing $GN_2$ from emerging from the cutting chamber and also preventing the cutting chamber from becoming heated.

Further developments of the invention reside in that a program selector switch makes it possible to preselect the optimum $LN_2$ tank filling for specific working conditions, by the use of a rotary switch or buttons, in such a way that upon progressive movement in one specific direction or rotary movement, the cooling effect is continuously increased. A function diagram illustrates by illuminated fields or LED displays the existing or preselected level of filling. The level of filling in the tank system is, via a microprocessor control unit, automatically adapted to the preselected values of the temperatures of the object support, the knife support and the chamber gas, the manually preselected or automatically predetermined working conditions being in turn indicated in a function diagram in the manner described.

BRIEF DESCRIPTION OF THE DRAWINGS

An apparatus according to the state of the art, as the premise on which the invention is based, and also examples of embodiments of the apparatus according to the invention are explained in greater detail hereinafter, with reference to the accompanying drawings, in which:

FIG. 16 is a diagrammatic sectional side view similar to FIG. 9 of a further embodiment of the invention with an additional angled separator tube to FIG. 9;

FIG. 17 is a diagrammatic sectional side view similar to FIG. 5 of a further embodiment of the invention with an $LN_2$ cooled covering over a gas heating plate, on which it is possible to deposit frozen specimens or preparation aids which are to be cooled;

FIG. 18 is a diagrammatic sectional front view similar to FIGS. 3 and 4 of a further embodiment of the invention with a modified assembly of a knife support and a chamber; and FIGS. 19A to 21 are diagrammatic views of further embodiments of the invention for the display and/or preselection of working conditions, FIGS. 20 and 21 being block diagrams.

DETAILED DESCRIPTION OF THE INVENTION

Figure 1:
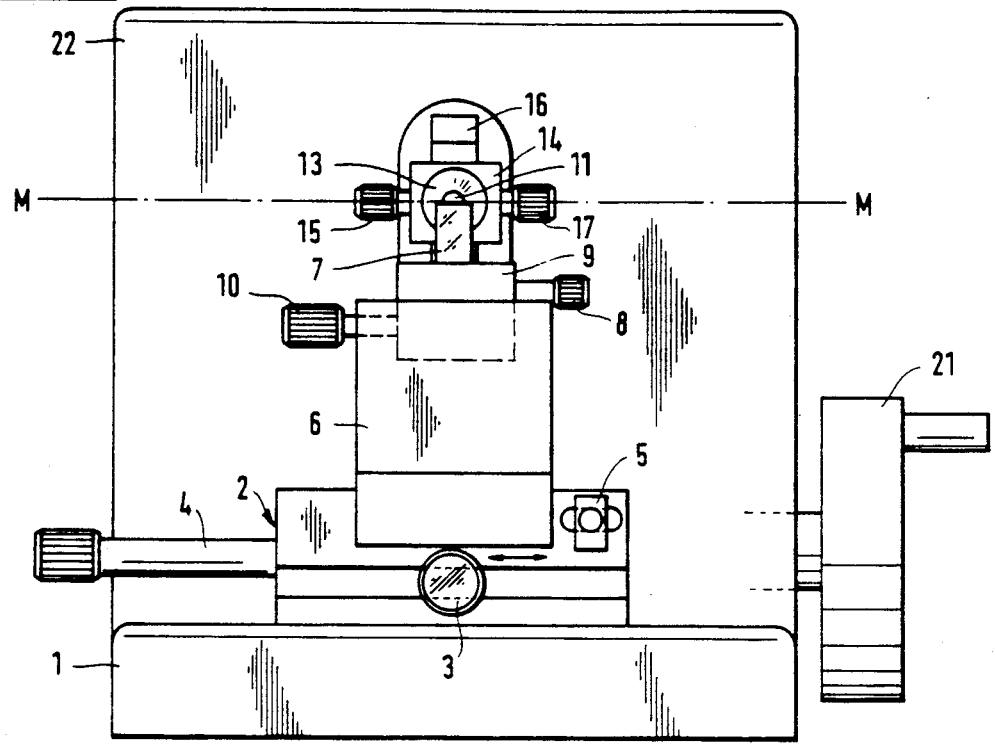
FIGS. 1 and 2 are diagrammatic front and side views of a series section or ultramicrotome for use at room temperature, with a fixed knife on a cross slide and with an upwardly and downwardly reciprocating object on a preparation carrier arm.
Figure 2:
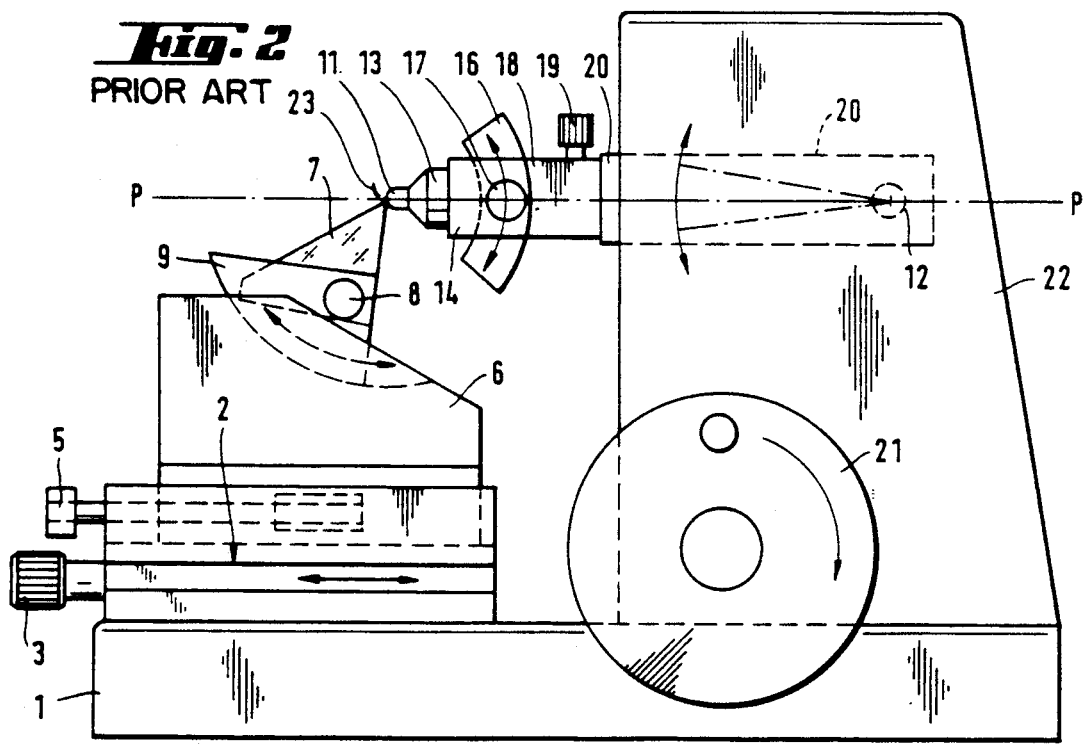
Figure 3:
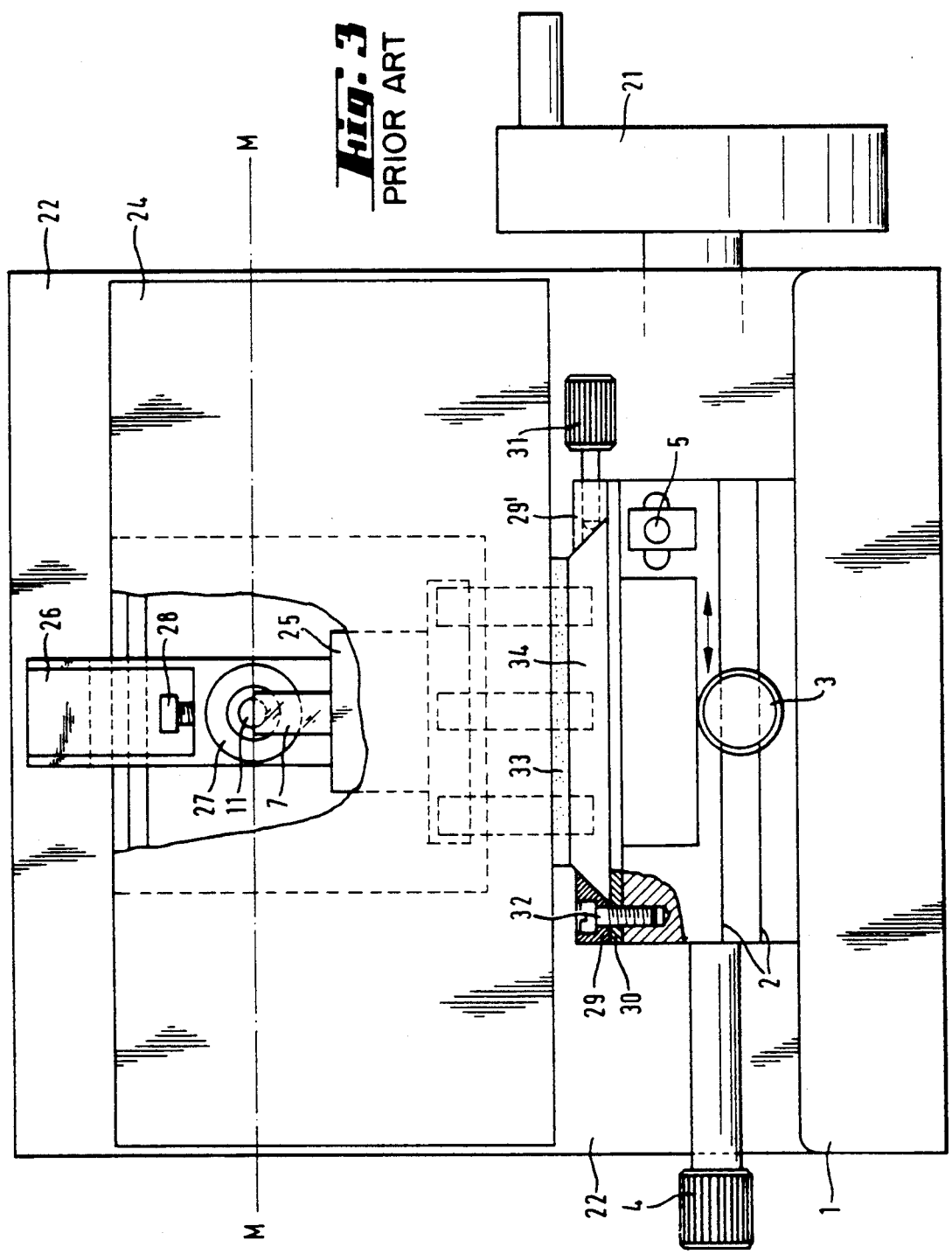
FIG. 3 is a diagrammatic partially sectioned front view of the cooling chamber according to the state of the art mounted on the knife cross slide of a microtome according to FIG. 1 (see also FIGS. 4 to 6) for preparing sections at reduced temperature.

Cooling chambers are mounted exclusively on rotary (also MINOT or serial section) microtomes or ultramicrotomes. Common to all these cutting instruments according to the state of the art, which are shown diagrammatically in FIGS. 1 and 2, is the fact that a knife support or carrier 6 mounted, for example, by means of a cam and via a clamping lever 5 on an instrument base 1 through a cross slide 2 (feed transmission 3, lateral displacement transmission 4) is disposed to be rigid except for movements of the support (see double-headed arrows) in contrast to carriage mounted microtomes. A knife (e.g. a glass cutter 7) is fixed by a clamping screw 8 in a pivotable part 9 which permits eucentric adjustment of an optimum blade angle and is in turn fixed on the knife carrier 6 by a clamping screw 10. In contrast to the fixed knife 7, either in the case of ultramicrotomes or semi-thin sectioning devices for producing microsections in the thickness range $\leq 1$ μm (see H. SITTE, Ultramicrotomy, mta-journal extra No. 10, Umschau-Verlag. 1985), an object 11 shown in FIG. 2 is moved upwards and downwards on a circular path about a bearing 12 or in the case of rotational microtomes for light-microscopy, will be moved upwards and downwards on a vertical straight path in a manner not shown. For the preparation of sections, the object 11 is clamped in a holder 13 rotatable about its longitudinal axis, which is in turn fixed, on a pivoting part 14 by a clamping screw 15 and, as shown in FIG. 2, is pivoted ia the direction of the double-headed arrow on a segmental arc 16 on a eucentric circular path and can in turn be mounted thereon by means of a clamping screw 17. The segmental arc 16 is in turn fixed by its holder 18 on a preparation carrier arm 20 by means of a clamping screw 19, the arm 20 being movable upwards and downwards by means of a handwheel 21, for instance via a cam control means not shown in FIG. 2 but disposed under a cover 22 of the microtome. FIG. 2 shows the preparation carrier arm 20 with an axis PP thereof in that horizontal position in which a section 23 is being taken by the cutting edge of the knife 7 from the object 11. An extension MM of the knife edge shown in FIG. 1 intersects the axis PP of the preparation carrier arm 20 in this position. For fitment of a cooling chamber (FIG. 3), both the knife support structure 6 to 10 which is provided for normal preparation of sections at room temperature is removed from the knife support cross slide once the clamping lever 5 has been slackened. Also once the clamping screw 19 has been slackened, the object support structure 12 to 18 can be removed from the preparation carrier arm 20. In place of these elements, as shown in FIG. 3, a cooling chamber 24 with a different kind of knife support 25 for the knife 7 are placed on cross slide 2, and a different kind of preparation holder 26/27/28 for the object 11 are fixed on the preparation carrier arm 20. Experience has shown that the clamping device 5 provided for the relatively small knife carrier 6 provides only an inadequate support for a large and heavy cooling chamber, the more so since it is almost inevitable that when preparation of the microsections is completed, a hand will come to bear on the outside wall of chamber. The lever forces which occur in consequence cannot be resisted by the clamping system 5 which is provided for normal operation. Therefore, more rigid assembly elements have been developed for mounting a cooling chamber on the cross slide 2 of a microtome, particularly of an ultramicrotome, for example the system shown diagrammatically in FIG. 3 and corresponding to the current state of the art, and which consists of a dovetail receiving element 29/29' with a baseplate 30 and a separate clamping screw 31 and which is rigidly connected to the cross slide 2 by screws 32. For the purpose of assembly, there is on the underside of a metal chamber wall 24 a flexible interlining 33 (e.g. soft rubber) on which there is an insertion tailpiece 34 which matches the receiving elements 29/29'/30/31/32, the connections between the elements 24/33 and 33/34 representing permanent connections by adhesion or by vulcanisation, if the mounting 33 consists of rubber. Compared with this soft connection between the tailpiece 34 and the cooling chamber wall 24, there is between the tailpiece 34 and the knife carrier 25 a rigid metal connection which has no resilient intermediate members, as described hereinafter with reference to FIGS. 4 to 6. The aim of this assembly which corresponds to the current state of the art was that any handling forces such as arise, for instance, when a hand is placed on the chamber wall 24, might be transmitted to the cross slide 2 in a diminished strength.

Figure 4:
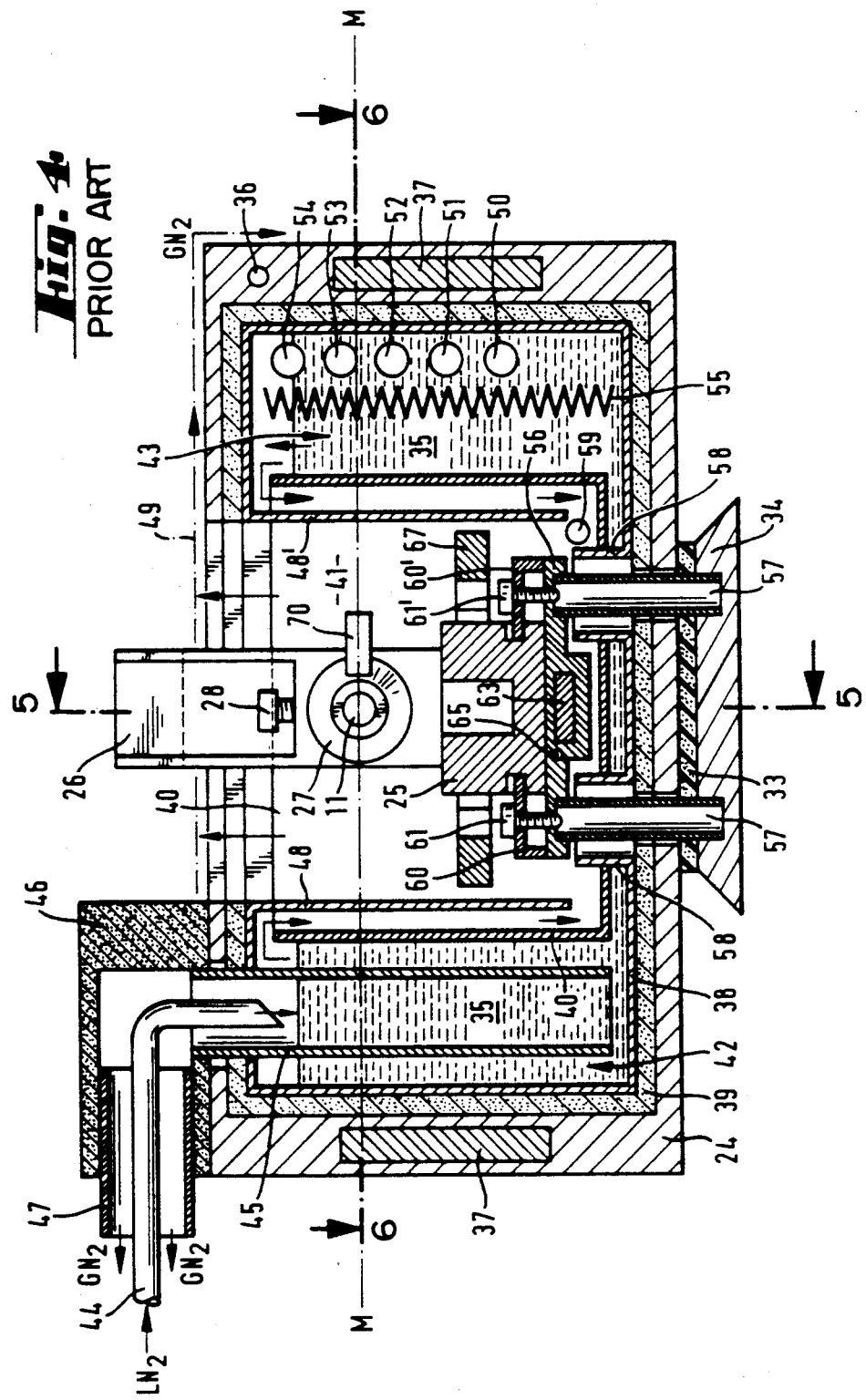
FIGS. 4 to 6 are diagrammatic views of the cooling chamber according to the state of the art as shown in FIG. 3, FIG. 4 being a sectional front elevation (along plane 4—4 in FIGS. 5 and 6, FIG. 5 being a sectional side view along plane 5—5 in FIGS. 4 and 6, and being a sectional plan view along plane 6—6 in FIGS. 4 and 5.
Figure 5:
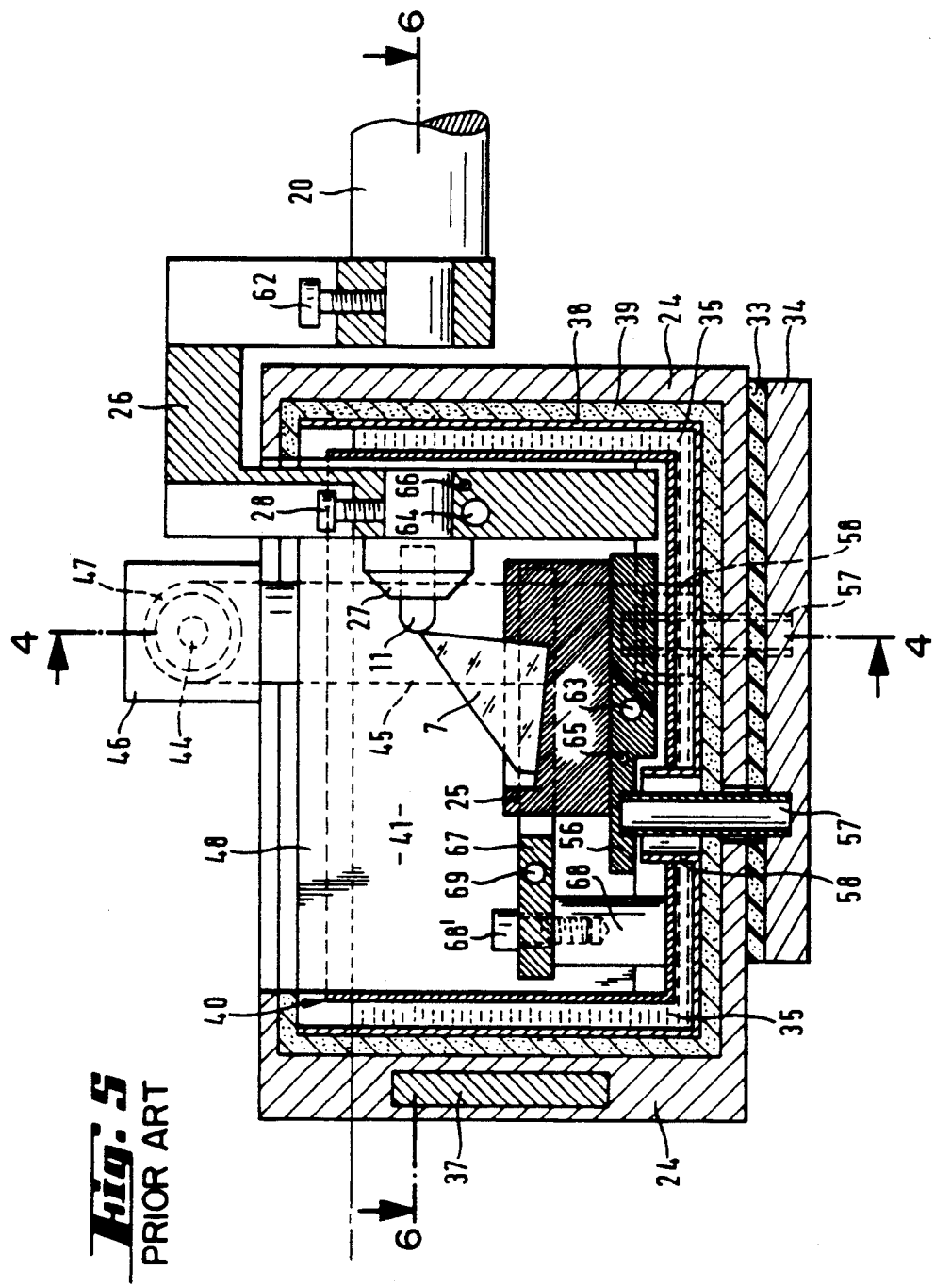
Figure 6:
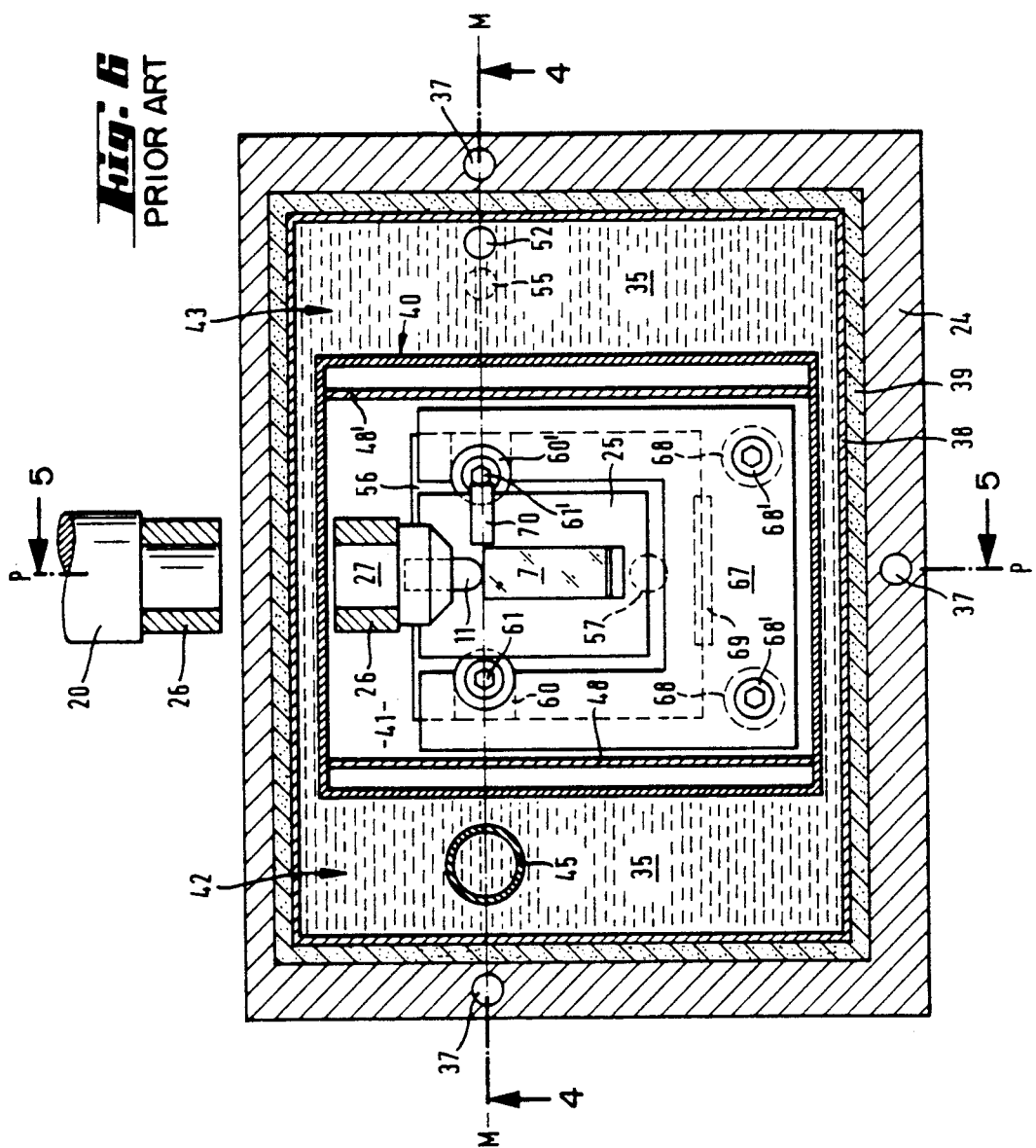

FIGS. 4 to 6 are diagrammatic views detailing the construction of a cooling chamber according to the state of the art, which is the premise on which the invention is based. Where a cooling chamber is to be used for preparing microsections in the total range of temperatures between $-190°$ C. as the minimum value given by the boiling point of $LN_2$ which is normally used as a cryogenic medium and a maximum value which is as close as possible to room temperature, such chamber as a rule, enclosed by a readily heat-conductive metal chamber wall 24 (of cast aluminum, for instance), the temperature of which is in known manner thermostatically maintained at room temperature (e.g. $20° \pm 5°$ C.) by a temperature sensor 36 and a plurality of heating elements 37 connected via an electronic unit (not shown). in this chamber wall 24 is an open-topped sheet metal tank 38 to hold $LN_2$ 35 and which is thermally insulated with respect to the heated chamber wall 24 by a foamed plastic insulation 39. In the sheet metal tank 38 there is a further open-topped sheet metal container 40, the walls of which define a cutting chamber 41. In consideration of the limited space available in the object-knife area of a microtome, particularly an ultramicrotome, the depth and height of the container 40 are such that only narrow spaces exist between the front and rear walls of the container 40 and the corresponding walls of the tank 38 as well as between the bottom of the container 40 and the bottom of the tank 38. If no excessive cooling demands are made or if minimum temperatures $\geq -170°$ C. at the level of the knife blade and adequate for the majority of jobs can be tolerated, then the spaces between the front and rear walls and between the bottoms of the containers 40 and of the tank 38 are unnecessary. $LN_2$ containers 42 and 43 (twin tanks defined) on opposite side of the cutting chamber 41 are in this case, which is not illustrated, connected by a pipe so that there is communication between the $LN_2$ in both containers. In the case of the cooling chamber shown in FIGS. 4 to 6, if $LN_2$ is passed through a filling pipe 44 into the $LN_2$ container 42, then $LN_2$ flows through the gap between the bottoms of the container 40 and of the tank 38 from container 42 into $LN_2$ container 43. When a minimum $LN_2$ level is reached, a separator pipe 45 of a "phase separator" blocks off ingress of $GN_2$ from the filling pipe 44 into the container 42 and, as the process continues, into the cutting chamber 41 just as conversely it prevents emergence of $GN_2$ from the container 42 into a $GN_2$ discharge pipe 47 of such separator. All the $GN_2$ evaporating from the $LN_2$ 35 into the $LN_2$ containers 42 and 43 is instead, as shown in FIG. 4 (arrows) deflected by deflecting elements 48/48' onto the bottom of the container 40, i.e. (cutting chamber 41 which is swept by the resultant upwardly directed stream of cold dry gas. In spite of the open top chamber construction, the cutting chamber 41 always receives this scavenging with $GN_2$ in a frost-free manner. The stream of $GN_2$ emerging from the chamber bottom at about $-190°$ C. becomes steadily heated as it moves upwardly through the cutting chamber 41 and at the open top thereof, depending on the level of $LN_2$ and the chamber construction, it will attain a temperature of between about $-130°$ and $-170°$ C. By virtue of the low $GN_2$ temperature, there is, as shown in FIG. 4, at the chamber opening an interface 49 between cold $GN_2$ and room air which is similar to a boundary between phases: upon passage through this relatively stable interface 49, one observes a temperature jump of about -150° to 190° C. The $GN_2$ which emerges constantly with an intensity of about 1 liter/second flows over the thermostatically heated chamber wall 24, becoming heated in the process to a temperature which no longer has a disturbing effect on the microtome, particularly an ultramicrotome mechanism. Topping-up is in a per se known manner controlled by an electronic device (not shown) via filling level sensors which are disposed in the calmer $LN_2$ container 43 which is not directly affected by the turbulence and fluctuations in the $LN_2$ level brought about by the phase separator structure 44 to 47. As shown in FIG. 4, thermosensitive diodes 50 to 54 or resistance thermometers 55 are used as such filling level sensors. For example, the diode 51 can start the operation of topping-up with $LN_2$ and the diode 54 can stop it again. The signals from the diodes 50 to 54 additionally permit a visual display of the level of filling (for instance by LED's) at a control unit.

Cooling chambers according to FIGS. 4 to 6 are, in the manner already described with reference to FIG. 3, generally mounted on the knife support structure of a microtome, particularly an ultramicrotome, by means of a clamping screw 31 and an assembly element 34. Accordingly, upon a feed or lateral movement of the cross slide 2, the entire chamber accordingly follows such movement. A baseplate 56 for the knife carrier 25 with the knife 7 is rigidly connected to the assembly element 34 by thin-walled tubes 57 which consists of a nom-readily heat-conductive alloy (e.g. special steel containing 35.5% Ni and 0.5% C), while between the chamber wall 24 and the assembly element 34, there is generally inserted the aforesaid resilient insert 33 which reduces the effect of handling forces. The tubes 57 traverse the bottoms of the container 40 and tank 38 through tubes 58 welded in place in $LN_2$-tight fashion and which project about 15 mm beyond the bottom of the container 40 into cutting chamber 41, so that for more rapid cooling of the baseplate 56 of the knife support, and of the object support, the bottom can be covered by about 10 mm depth of $LN_2$. This is achieved, for example, by switching over the stop function to the measuring diode 59 (see FIG. 4). The knife carrier 25 is connected to the baseplate 56 in a separable force-locking manner by means of two clamping levers 60/60' and the clamping screws 61/61'.

Nowadays, the object 11 fixed in a rotatable object holder 27 is almost exclusively mounted on a "bridge" 26 by means of a clamping screw 28, using the CHRISTENSEN (1.c.) arrangement. The bridge 26 is in turn, as shown in FIG. 5, mounted by a screw 62 on the preparation carrier arm 20 of the microtome, an ultramicrotome. Therefore, during microsection preparation, the object 11 follows the upwards and downwards movement of the preparation carrier arm 20. Along with the mechanical elements, each cooling chamber of the type described comprises heating elements (e.g. heating cartridges) for heating up the knife support 25/56, the object support 26/27 and the $GN_2$ scavenging gas. In the carrier elements 56 and 26, for example, there are heating cartridges 63 and 64 for raising the knife and object temperatures beyond those levels which result from heat absorption (e.g. via the tubes 57 or the bridge 26) and the heat given off to the $GN_2$ scavenging gas in the steady state. In addition, temperature sensors 65 and 66 are used for measuring the resultant temperatures or for regulating these temperatures to preselected levels by means of an electronic unit, not shown. To increase the temperature of the $GN_2$ current which is above all vital to the cutting temperature, in the case of cooling chambers of the type described, a "gas heating plate" 67 is used in the state of the art and is fixed to the bottom of an container 40 via the assembly element 68 and can be heated by a heating cartridge 69. The effect of this gas heating plate 67 is checked by a temperature sensor 70 which measures the temperature of the $GN_2$ scavenging gas at the level of the edge of the knife 7 and is, as shown in FIGS. 4 or 6, disposed in the cutting chamber 41 directly alongside the knife (assembly elements are not shown).

As already mentioned, the system according to the state of the art, as described with reference to FIGS. 4 to 6, has a number of serious disadvantages. These drawbacks include above all the fact that it is impossible to raise the temperature of the $GN_2$ scavenging gas in the object-knife zone above $-80°$ C. Furthermore, it is disadvantageous that in the temperature range around $-100°$ C. which is mostly used, the consumption of $LN_2$ is substantially twice that which is consumed in the more rarely required low temperature range of $\leq -160°$ C. This difference in $LN_2$ consumption, at around 3.5 liters $LN_2$/hr, is so high that with the currently normal $LN_2$ price of around 7.- Austrian schillings per liter of $LN_2$, and the frequently necessary continuous working rate of 8 hours per working day or around 1600 hours/working year, the additional cost involved is about 40,000 Austrian Sch. per working year which is already more than 10% of the investment costs of such a cooling chamber system. Finally, the pressure waves which occur at the onset of topping-up, due to boiling processes, result in wave movements in the $LN_2$ in the tank system which, by secondary boiling processes, lead to a surging release of $GN_2$ in the twin tanks and, as the process continues, to a failure of some microsections. In conclusion, mounting of the heavy and bulky chamber on the knife cross slide has proved to be disadvantageous, since the handling forces resulting, for example, from hand pressure when removing the microsections, can influence the position of the knife cross slide and often make it necessary to readjust the relative positions of the object-cutting surface and the knife edge, not to mention frequent faults with the high-precision cross slide.

Figure 7:
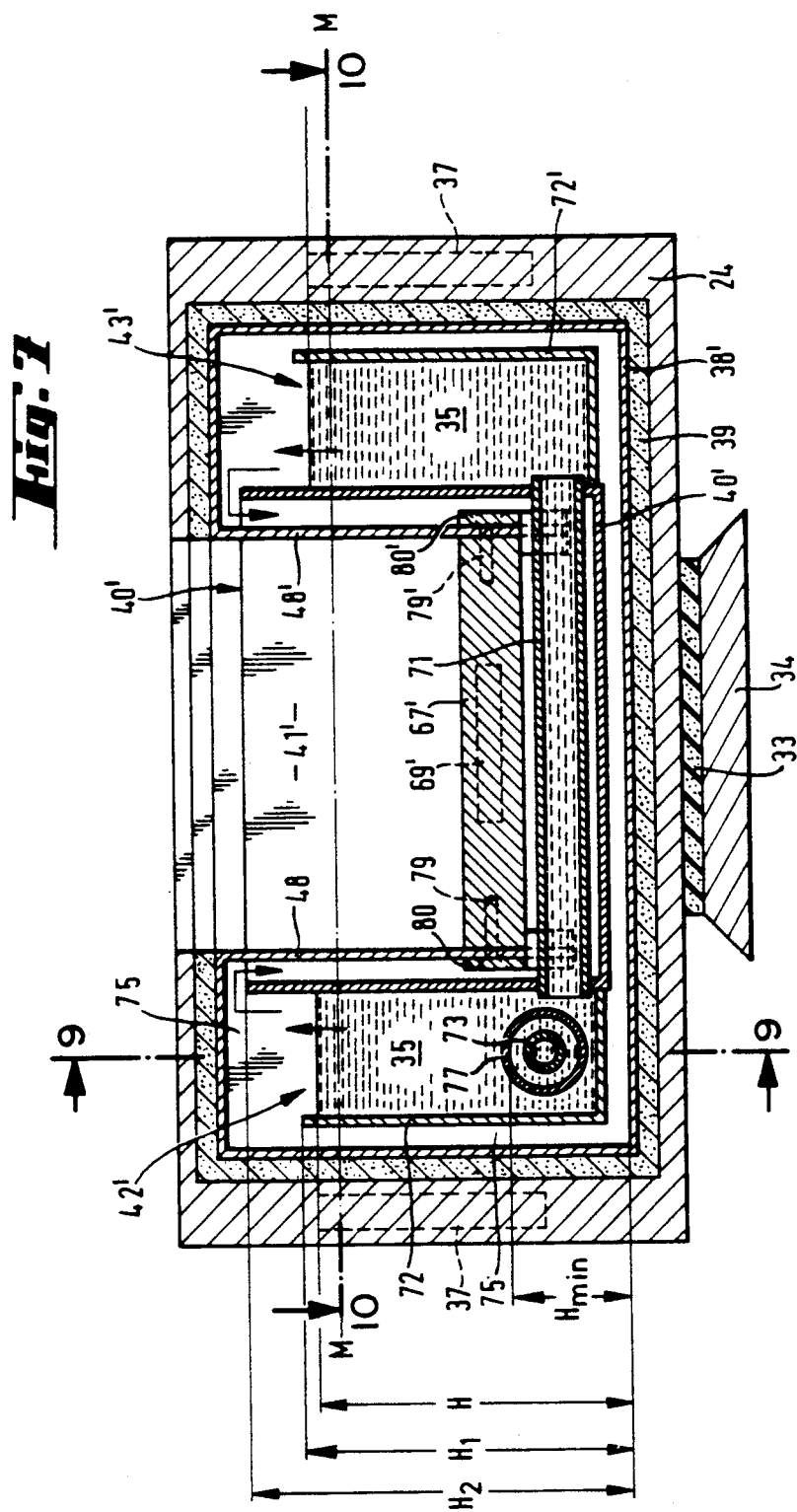
FIGS. 7 to 10 are diagrammatic views of the basic construction of a first embodiment of a cooling chamber according to the invention with undivided inserted tanks, separator chamber and gas heating plate, FIGS. 7 and 8 being sectional front views for different levels of $LN_2$ filling in a simplified illustration without a cutter or object support and separator connections (FIG. 7 with $LN_2$ filling at level $H < H_1$ and FIG. 8 with $LN_2$ filling at the level H at $H_1 < H < H_2$, both along the section plane 7, 8-7, 8 in FIG. 10), FIG. 9 being a sectional side view along sectional plane 9—in FIGS. 7 and 8 and showing an $LN_2$ filling level similar to FIG. 7, and FIG. 10 being a sectional plan view along section plane 10—10 in FIGS. 7 and 8 showing an $LN_2$ filling level similar to FIG. 7, FIGS. 11 to 13 are diagrammatic views of a further embodiment of the invention with sub-divided inserted tanks, FIGS. 11 and 12 being sectional front views for different levels of $LN_2$ filling and FIG. 13 being in a sectional plan view similar to FIG. 10.
Figure 8:
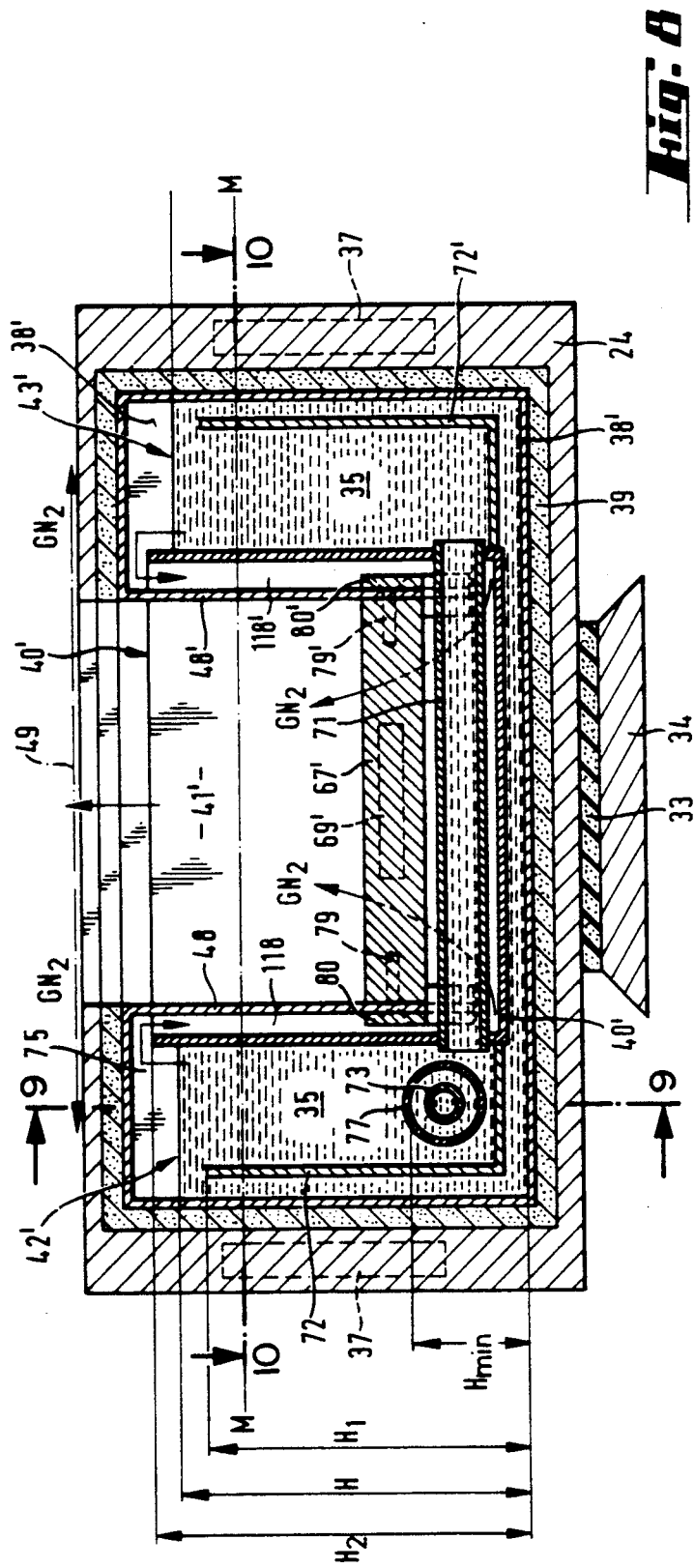
Figure 9:
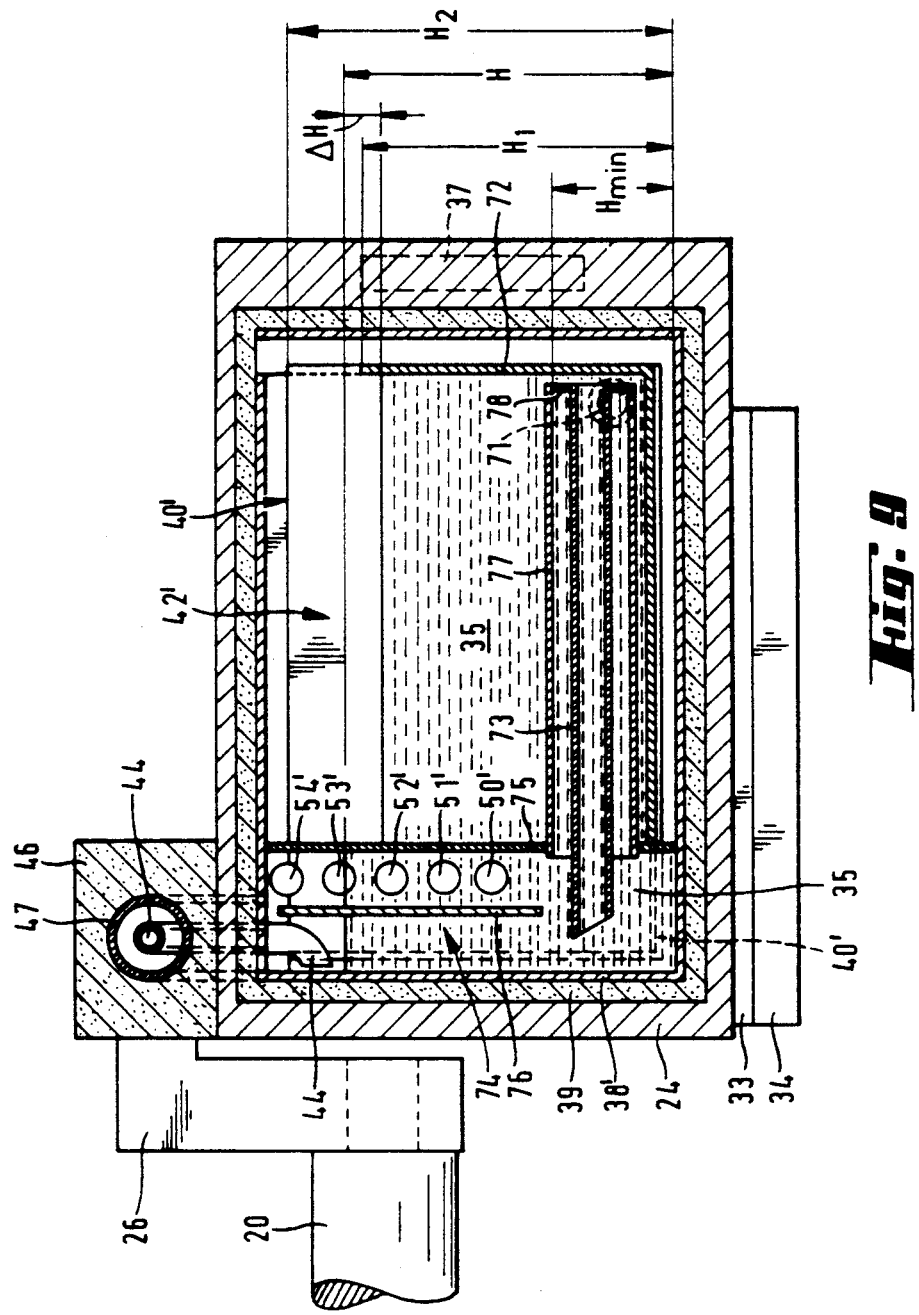

All of these disadvantages can be satisfactorily overcome, and at negligible extra cost, by the system according to the invention, which is shown in FIGS. 7 to 18. In the drawings described hereinafter, identical or equivalent parts are identified by the same reference numerals (though with an added apostrophe), as in FIGS. 1 to 6. According to FIGS. 7 to 10, the initially mentioned disadvantages of systems according to the current state of the art can be substantially overcome by using two symmetrically disposed inserted or additional tanks 72, 72' which communicate by a separate tank connection 71, by means of the tank system 38'/40'/72/72' which in the $GN_2$ range is completely isolated and in the $LN_2$ range is connected by just a narrow-gauge, preferably at least 80 mm long connecting tube 73 of relatively small diameter (for instance an inside diameter about 3 mm) to a separator tank which is constructed as a separator chamber 74 by a partition 75, and by means of a modified mounting of gas heater plate 67' on baffles 48/48'. In this case, a left-hand $LN_2$ tank 42' as shown in FIG. 9 is divided by the partition 75 into two compartments substantially in a ratio $\leq 1:4$, the smaller compartment serving as separator tank 74 which is connected to the rest of the tank system 38'/40'/72/71/72' just by the relatively long and narrow gauge horizontally disposed separator tube 73 which under normal operating conditions is constantly below the $LN_2$ level and is therefore filled with $LN_2$. The left-hand $LN_2$ container 42' which is adjacent the separator chamber 74 and also the right-hand $LN_2$ container 43', apart from the two inserted tanks 72/72', correspond to the $LN_2$ tanks 42 and 43 in FIG. 4. Once again, topping-up with $LN_2$ is controlled by level sensors (e.g. thermosensitive diodes 50' to 54') which, for example, as shown in FIG. 9 may be disposed in the separator chamber 74 behind a splash guard 76. The function of this apparatus is such that, upon the first filling of the separator chamber 74 with $LN_2$ 35, the level of $LN_2$ must initially reach a minimum height $H_{min}$ so that the separator tube 73 is entirely flushed with $LN_2$ and is therefore cooled to $LN_2$ temperature, since $LN_2$ cannot by reason of the boiling processes which start at once, flow out through a warmer tube of smaller diameter. In order to guarantee this, therefore, the separator tube 73 is enclosed by a tube 77 of larger diameter (e.g. 10 mm clear diameter), the free end of which is closed by a thin-gauge cover 78 to which the separator tube 73 is fixed and is open-ended. When the $LN_2$ height $H_{min}$ is reached, the tube 77 is entirely filled with $LN_2$ and the separator tube 73 is therefore cooled by $LN_2$, so that now $LN_2$ can flow through the separator tube 73 into the inserted tank 72 and thence through the connecting tube 71 into the corresponding right-hand inserted tank 72'. The separator system according to the invention, as described, prevents wave motion in the tank system 42'/43' which is completely separated by the partition 75, in that temporary $GN_2$ pressure fluctuations can scarcely be propagated by the column of liquid in the relatively narrow gauge and long separator tube 73, the conditions in the tank system 42'/43' being scarcely open to change by a brief and negligible acceleration of the $LN_2$ motion in this tube Further filling can be controlled in known manner, for instance by the diodes 50' to 54'. This control can, for example, ensure that the $LN_2$ level in the inserted tanks 72/72' always remains below the height $H_1$ of the walls of the inserted tanks. Since discharge of $LN_2$ over the upper edges of the inserted tank walls is impossible, the situation shown FIGS. 7 and 9 results: the $LN_2$ filling is, other than the separator tank 74, restricted to the two inserted tanks 72/72' and the tube 71 which connects them. The level of $LN_2$ in the separator tank 74 is thereby always somewhat above the level in the inserted tanks 72/72', for example by the amount $\Delta H$ shown in FIG. 9. In this example, topping-up can be started by the diode 51' and stopped by the diode 53', which is disposed at the height $H_1$ of the top edges of the side walls of the inserted tanks 72/72'. In contrast, upon a switchover of the starting function to the diode 52' and of the stop function to the diode 54', the $LN_2$ level would exceed the height $H_1$ and so cause $LN_2$ to flow out of the inserted tanks 72/72' into the twin tanks formed by the walls of the sheet metal containers 38' and 40'. The resultant situation as shown in FIG. 8 is like that in FIGS. 4 to 6, since now the walls of the inserted tanks 72/72' are nonfunctioning. The same applies to the situation which results from a switchover of the operation to the diodes 54' (start, see FIG. 9) and 59 (stop, see FIG. 4) and which corresponds to overfilling of the tank system shown in FIGS. 4 to 6, which is used for rapid cooling of the object and knife supports.

This possibility corresponds to the current state of the art and is therefore not illustrated again in FIGS. 7 to 10. The $LN_2$ level then attains a uniform height $\geq H_2$, $H_2$ corresponding to the height of the lateral boundary walls of the sheet metal container 40'. Consequently, $LN_2$ flows out into the cutting chamber 41' until $LN_2$ wets the diode 49. Conversely, by switching the topping-up control back to the diodes 50' (start) and 51' (stop), it can be ensured that a smaller part of the wall area of the sheet metal container 40' is directly cooled by $LN_2$. Under this condition, the cooling effect and the flow of $GN_2$ scavenging gas can be considerably reduced, so that without any expensive accessory measures, a steady state can be brought about which makes it possible to prepare microsections at relatively high temperatures.

Figure 10:
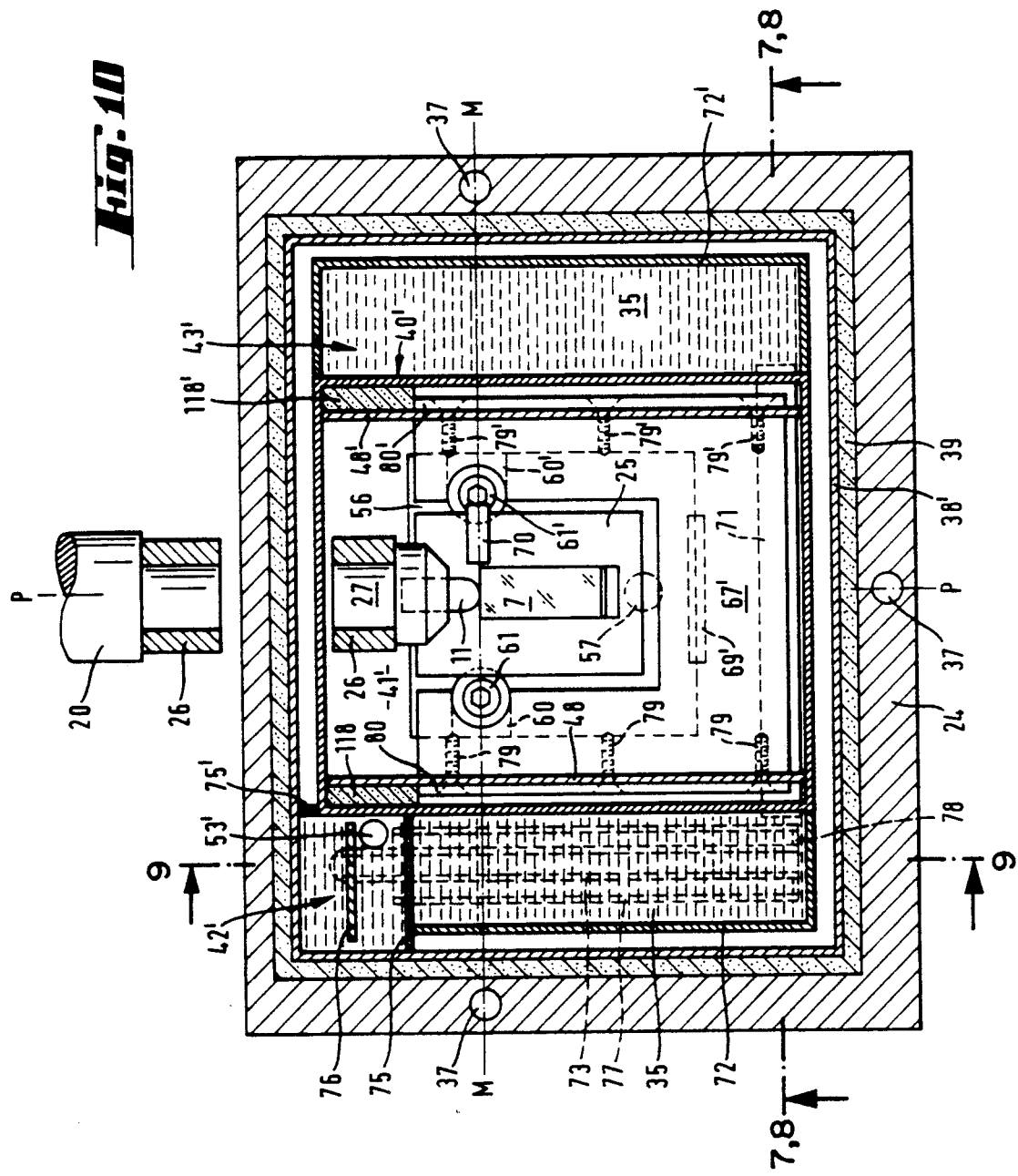

As an additional device for controlling or regulating the temperature of the $GN_2$ scavenging gas in the cutting chamber 41', there is provided, as shown in FIGS. 7, 8 and 10, a gas heating plate 67'/69' which in contrast to the state of the art (see FIGS. 4 to 6) is not thermally connected by an assembly part 68 to the walls of the container 40' but by screws 79/79' and profile sections 80/80' to the deflecting baffles 48/48'. Any direct thermal contact which can lead to a disturbing increase in $LN_2$ consumption as a result of a direct solid state heat flow, such as occurs in the state of the art, shown in FIG. 5, is thus avoided. In contrast, optimum heat exchange takes place between the surfaces of the parts 48/48'/80/80' and 67' and the $GN_2$ scavenging gas which for equal strength or velocity of gas flow becomes heated to the desired temperature with a considerably reduced heating output. The properties described can be effectively assisted by two inserts 118/118' which consist of a thermally insulating material (for example, foamed polystyrene or polyurethane) which are disposed on either side of the bridge 26 between the walls of the sheet metal container 40 and the flecting baffles 48/48' in such a way that the total quantity of $GN_2$ scavenging gas escaping from the tank system 38'/40'/72/72' is passed through the profile sections 80/80' and the gas heating plate 67' (see FIGS. 8 and also 10 to 12).

Figure 11:
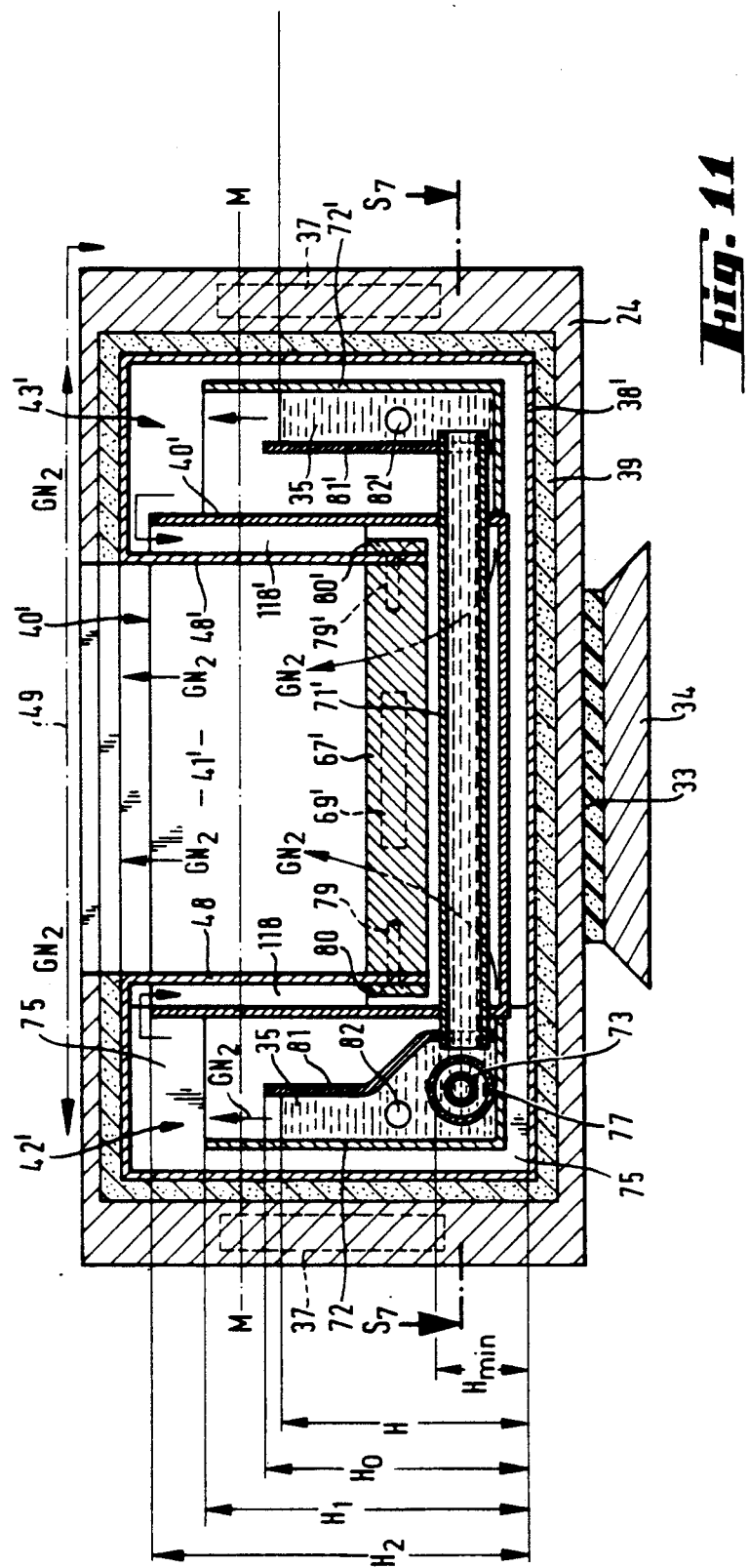
Figure 12:
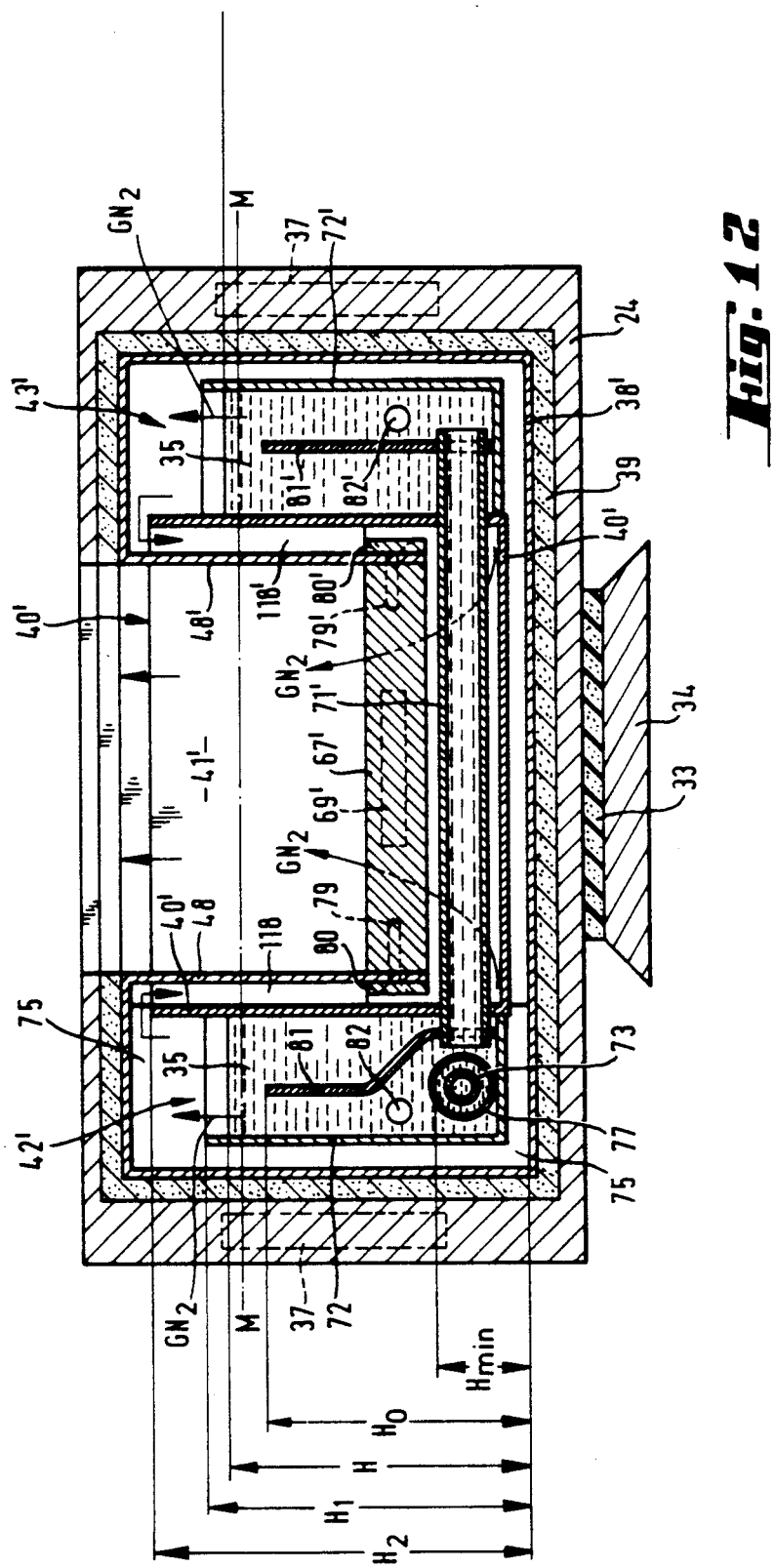
Figure 13:
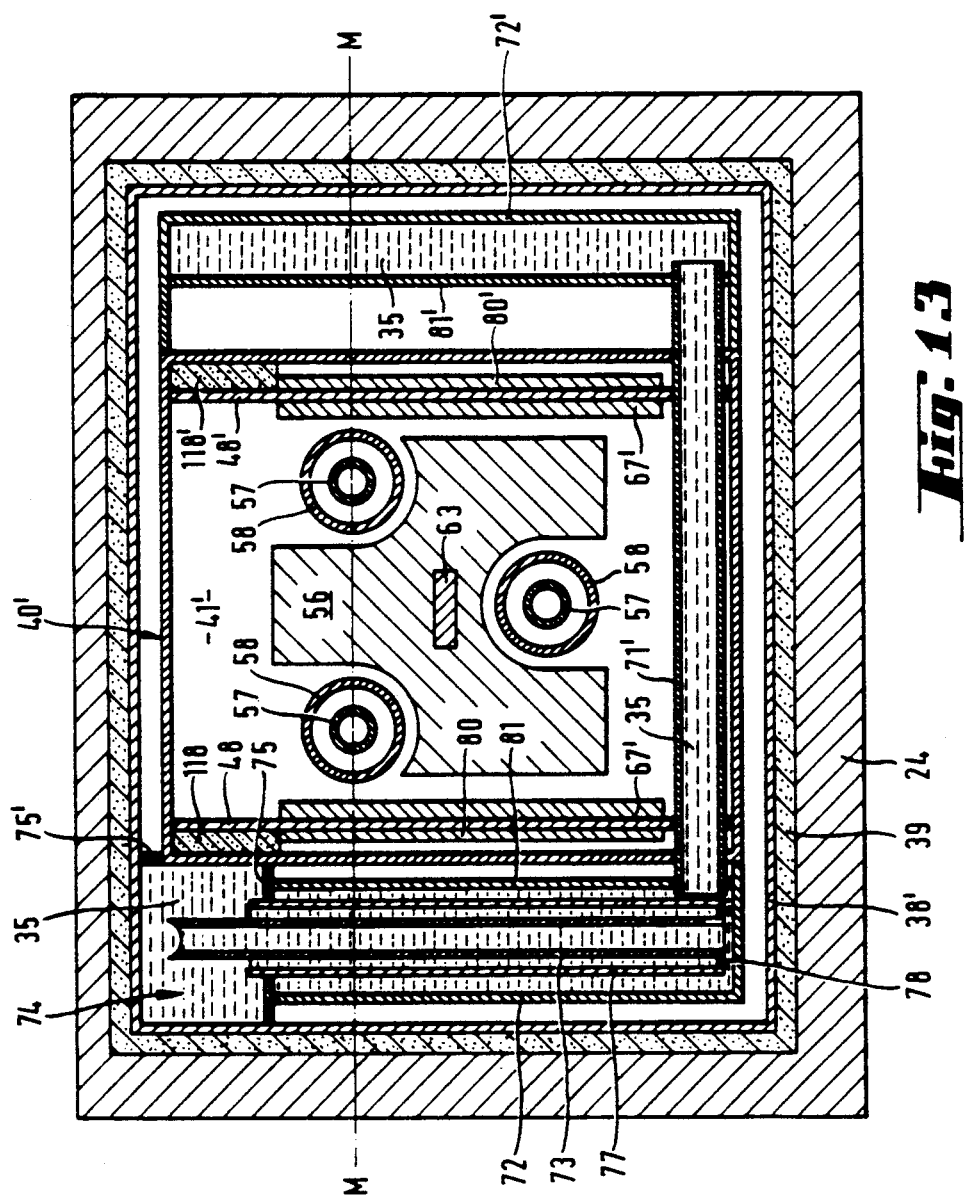

A further development of the invention for operating cooling chambers in the range between room temperature and about $-40°$ C. is made possible without forgoing the advantages of operation in the medium and ultra-low temperature ranges and without any noteworthy extra cost if the tank system is constructed as shown in FIGS. 11 to 13, wherein inserted tanks 72/72' are, by additional predominantly vertically orientated partitions 81/81' disposed parallel and symmetrically with respect to the plane of symmetry of the chamber, into in each case two compartments, the two outer compartments being connected to each other by connecting tube 71' which extends as far as the partitions 81/81'. The separator tube 73 with its sheathing 77/78 projects into one of the compartments formed by the partitions (e.g. partition 81) and fills with $LN_2$ firstly this compartment and then the compartment on the other side which is linked thereto by the connecting tube 71', as shown in FIG. 11 and in FIG. 13. To accommodate the tube 77, the partition 81 can, for instance, be so angled that for approximately the same volume of the two compartments on the right and left the tube 77 can be accommodated in the bottom half of the left hand outer tank 72/81. So long as a level of $LN_2$ is maintained below the height $H_0$ which is the height of the partitions 81/81', LN₂ does not come into direct contact with any part of the wall of the sheet metal container 40' apart from the wall of the separator tank 74. Cooling therefore takes place with a cooling effect which is again considerably reduced in comparison with the system according to FIGS. 7 to 10 and is effected solely via the bottom and side portions which consist of sheet metal and which are disposed between the outer compartments of the inserted tanks 72/72' and the walls of the container 40'. This cooling can, in the manner described above, be adapted under control to working requirements by the choice of the thickness of the sheet metal and of the alloy used for the inserted tanks 72/72'. If the LN₂ level is varied to a height H within the limits $H_1 > H > H_0$ by switching over the control means, then LN₂ will flow out of the outer into the inner compartments of the inserted tanks 72/72' and the situation shown in FIG. 12 is established. Since in this case the separating walls 81/81' cease to be functional, the operating conditions now correspond to the simpler construction of system according to the invention, as described with reference to FIGS. 7 to 10. The same applies to the working conditions resulting from a further raising of the LN₂ level to heights H with the limits $H_2 > H > H_1$ and $H \geq H_2$.

By limiting the filling of LN₂ to the outer compartments of the inserted tanks 72/72' shown in FIG. 11 and FIG. 13, formed by the partitions 81/81', not only is the cooling effect reduced but to a great extent the LN₂ consumption is also substantially reduced. Thus, as matters proceed, also the flow of GN₂ scavenging gas will be reduced or the mean GN₂ velocity will be constricted. In extreme situations, this can mean that by reason of inadequate GN₂ sweeping or if the GN₂ temperature is excessively high, there is no longer a guarantee that the open topped cutting chamber 41' will enjoy freedom from frost. A further development of the invention provides a simple remedy for this drawback in that there are in the outer compartments of the inserted tanks 72/72' heating elements 82/82' (e.g. heating cartridges) which, as they give out their heat, give off additional GN₂ scavenging gas which, when required, can be heated by the gas heating arrangement 67'/69' to the desired temperature in the manner already described above.

Figure 14:
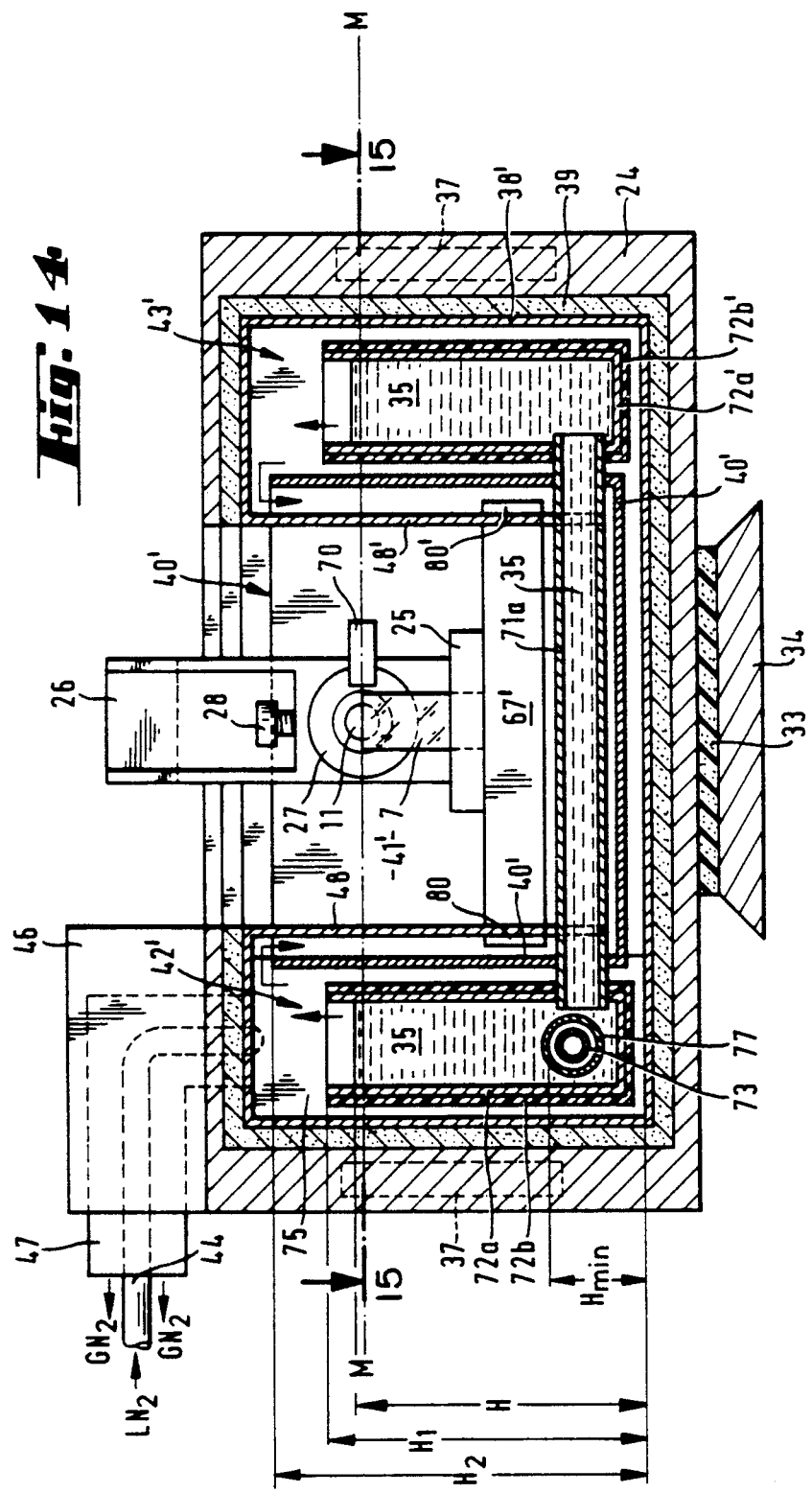
FIGS. 14 and 15 are diagrammatic views of a further embodiment of the invention with inserted tanks which are connected to the walls of a cutting chamber only by an $NL_2$ connecting tube and walls of a separator tank, FIG. 14 being a sectional front view similar to FIG. 11 and along section plane 14—14 FIG. 15, and FIG. 15 being a sectional plan view similar to FIG. 10 and along section plane 15—15 in FIG. 14.
Figure 15:
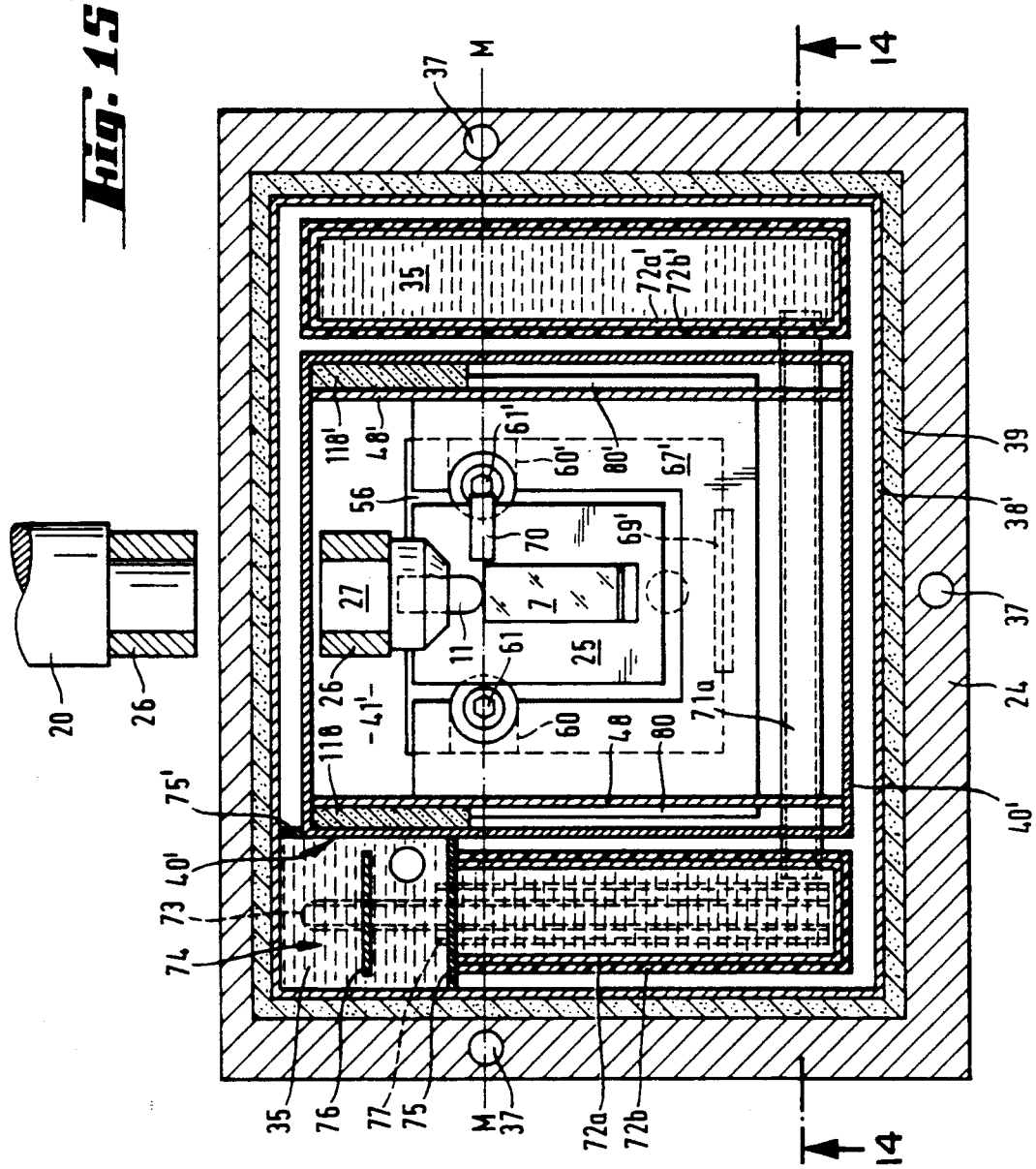

A particularly advantageous embodiment of the invention can, as shown in FIGS. 14 and 15 reside in that inserted tanks 72a/72a' are rigidly connected solely to the walls of the separator tank 74 and to the connecting tube 71a which connects these inserted tanks, there being furthermore no direct metallic connection to the side walls of the sheet metal container 40'. Therefore, apart from the walls of the separator tank 74, it is only at the assembly points (e.g. welded seams) of the tube 71a that the sheet metal container 40' comes into thermal contact with LN₂ 35, so long as the level H of LN₂ remains below $H_1$. The LN₂ consumption of this particularly simple and therefore cost favorable embodiment of the invention is therefore, with this type of operation where $H_{min} < H < H_1$, is particularly low, without any need to sacrifice the advantages of low temperature operation with conditions $H_1 < H < H_2$ and $H > H_2$ if the LN₂ level rises to the height H, as have already been explained with reference to the FIGS. 7 to 13. With this embodiment, if a further reduction in LN₂ consumption is required for operation at particularly high temperatures, in the region between about −20° C. and room temperature, then the inserted tanks 72a/72a' can be provided on their outer surfaces with a heat insulation 72b/72b' which may consist of a foamed synthetic plastic material (e.g. foamed polystyrene or polyurethane).

Upon transition from operation in the medium temperature range with inserted tanks 72/72' according to FIGS. 7 and 9 to 10, or with the inserted tanks according to FIGS. 11 to 13 divided by partitions 81/81', or with the inserted tanks 72a/72a' separated by sheet metal container 40' according to FIGS. 14 and 15, when the chamber is operated in the low temperature range (see FIG. 8), there is always a substantial increase in cooling output and thus also in the LN₂ consumption of the chamber. Under certain design conditions, it can happen that the throughput of LN₂ through the thin and long separator tube 73 no longer corresponds to the LN₂ consumption of the completely filled twin tank system 38'/40'. According to FIG. 16, within the framework of a further development of the invention, this problem can be overcome without any substantial extra cost by providing a second angled separator tube 83, without the manufacture of the chamber being rendered particularly complicated or expensive as a result. The second separator tube 83, like the separator tube 73, is disposed in large-gauge tube 77' and is fixed to thin-walled cover 78'. It extends within the tube 77' parallel with the separator tube 73 but is, however, angled upwardly in the separator tank 74 and has an end open at a height $H_x$ within the limits $H_1 < H_x < H_2$. This means that by virtue of this angled separator tube 83, LN₂ flows firstly out of the separator tank 74 through the inserted tank 72 into the rest of the tank system 38'/40' but not until the LN₂ level exceeds the height $H_x$. Corresponding to the higher consumption of LN₂ in the low temperature range, therefore, also the discharge of LN₂ from the separator tank 74 into the tank system is increased without any need to alter the dimensioning of the separator tube 73 which is desirable for operation of the chamber in the medium and high temperature ranges, having regard to as continuous and slow as possible a discharge of LN₂.

For heating of the GN₂ scavenging gas by the gas heating arrangement 67'/69', then also in the case of the assembly 79/80/80'/79' which according to the invention is modified with respect to the state of the art, under extreme operating conditions, particularly with additional release of GN₂ scavenging gas due to the heating elements 82/82', so much heat is given off at the baffle plates 48/48' shown in FIG. 7, due to the heating element 79' that the plate 67' attains temperatures which are considerably in excess of 0° C. In the case of cryo preparations, since there is often a need for space on which to place frozen biomedical objects 11, but since the gas heating plate 67' according shown in FIG. 10 occupies virtually all the repository area available, there are considerable problems in practical operation working. These problems can easily be resolved by a further development of the invention as shown in FIG. 17 in that there is thermally and mechanically coupled to the connecting tube 71, 71' or 71a which, under all the indicated working conditions of the cooling chamber according to the invention, as shown in FIGS. 7 et seq., is constantly filled with LN₂ 35, a profile 84 of readily heat conductive metal (e.g. aluminum) to which in turn is fixed a readily heat conductive plate 85 (e.g. likewise of aluminum), for example by means of a screwed connection 86 which is at a distance A (e.g. about 3 mm) above the upper surface of the gas heating plate 67' so that it has no solid contact therewith. Since the plate 85 is cooled by LN$_2$ 35 via the solid contacts 71'/84 as well as 84/86/85, then without any additional measures !' it will in any case attain a temperature in the range $< -100°$ C. which will be adequate for the majority of operations. Lower temperatures can be attained by increasing the thickness B of the sheet metal or by providing a foamed insulation 87. Finally, LN$_2$ losses can be limited by providing the profile element 84 with a foamed insulation 88.

According to FIG. 18, a further development of the invention may reside in that only the knife support 56/57 is rigidly connected to the cross piece 2 via an assembly element 89 corresponding to the knife carrier 6 in FIGS. 1 and 2 and, like the knife carrier 6, mounted on the cover plate of the cross slide 2, for example by means of an eccentric clamping lever 5, so that it performs the movements caused by the transmissions 3 and 4. However, in contrast thereto, the chamber walls 24 rest on the base 1 of the microtome, particularly the ultramicrotome, via lateral ribs 24', the relative position of the chamber walls 24/24' to the base 1 being predetermined and then maintained by a force-locking rigid connection of the two elements 1 and 24/24', for example bolts 90 and a clamped or screwed union (not shown). This development according to the invention is in particular characterised in that the assembly element 89 remains in a permanent force-locking connection with the cooling chamber by a support, for example angled members 92/92' which are fixed to the chamber wall 24/24' by screws 91/91' even when the cooling chamber is removed from the microtome, particularly the ultramicrotome, so that complicated fitting and dismantling operations are not required when the chamber is mounted on the microtome or when the two units are separated from each other. Apart from simplifying the assembly and dismantling of the cooling chamber which is achieved according to the invention, this arrangement above all permits an electrical connection of the heating cartridge 63 required for setting or regulating the knife temperature and that of the temperature sensor 65 inside the cooling chamber (see FIGS. 4 and 5). Furthermore, inserts 93, and 94 which are connected to the assembly element 89 prevents any discharge of GN$_2$ through the now enlarged passage 58' between the walls of the two metal tanks 38' and 40'. In this respect, an upper flat surface of the assembly element 89 is intimately connected to insert 93 for example a highly resilient layer of foam (e.g. soft rubber foam or foamed Moltopren(®)) in turn connected in the same way to a metal plate forming 94. The matching surfaces on the top of the plate 94 and on the underside of the chamber wall (flat milled surface 97) are so machined that by virtue of their precise plane-parallel nature and by their minimum surface roughness, they ensure an adequate GN$_2$ seal at the bottom of the cutting chamber 41' while sliding one on the other in a virtually friction-free fashion. By virtue of the intimate contact with the surface 97 of the chamber wall 24/24', the plate 94 assumes a temperature which is close to the temperature of the thermostatically heated chamber wall 24/24'. In order to achieve a lastingly force-locking contact between the matching plane surfaces 97 and 94, a distance D$_2$ between surface 97 and upper surfaces of angled members 92/92' is so dimensioned that either the resilient insert 93 still remains compressed even after the cooling chamber has been removed from the cutting means, or that spring elements (e.g. coil springs 93' disposed around the sleeves 57) maintain force-locking contact between the surface 97 and the upper plane surface of the plate 94. With regard to minimal friction of the surfaces 94/97, it is possible, for example, to envisage the insert 93 being compressed by about 1 mm when the chamber is fitted, so that the thickness of the layer 89'/93/94 which is held between the angled members 92/92' is reduced from D$_2$ to D$_1$ (D$_2$–D$_1$ ~ 1 mm). Apart from the heat resistance of the foamed insert 93, a greater heat transfer is prevented by the foamed insulation 96 between the chamber wall 24 and tank insulation 39 as well as by foamed insulation 98 which rests loosely on the passage 58', the insulating panels 96/98 being entrained by the tubes 57 in the fashion of a crank guide upon movement of the cross slide 2. Entrainment of the metal plate 94 upon movement of the cross slide 2 is brought about in a similar manner, for example by two pins or bolts 95/95' placing the insert profile of the assembly element 89 into the receiving profile on the cover plate of the cross slide 2 can be substantially simplified by suitable markings on the parts 89 and 92/92' in conjunction with bevelled surfaces on the bottom longitudinal edges of the element 89. The position of the assembly part 89 in relation to the chamber wall 24/24' or to the supports 92/92', which can be preselected by using the markings, can be so chosen that it corresponds to the position of the receiving profile in the cover plate of the cross slide 2 when this latter is in the "neutral" position, in other words has not been moved in any direction by the transmissions 3 or 4. This position corresponds to that illustrated in FIGS. 1 to 3 and 18.

Finally, further developments of the invention may serve to help the user control the most favourable operating conditions without having detailed knowledge and/or to keep him informed at all times concerning the particular conditions under which the system is operating. Thus, it is possible that those portions of the tanks which are filled with LN$_2$ or which have to be filled according to a selected program, as shown in FIGS. 19A–19B, may be indicated by an LED display or by being illuminated. Thus, in FIG. 19A, only the outer compartments of the inserted tanks 72/72' and the connecting tube 71 are filled with LN$_2$, which corresponds to the operating condition shown in FIG. 11. FIG. 19B shows both inserted tanks 72/72' completely filled, while FIG. 19C shows the entire twin tank assembly 38'/40' 40' filled. Finally, FIG. 19D shows a part of the cutting chamber 41' filled as far as the measuring diode 59, the filling being in each case LN$_2$, so that direct cooling with LN$_2$ of the knife holder base 56 and of the object support 26/27 will be achieved. As shown in FIG. 20 and in accordance with a preferred feature of the invention, it is possible manually to preselect these working conditions regardless of the preselection of temperatures at the currently generally used adjusting elements, for example by rotary knobs 99 (knife temperature ... T$_K$), 101 (object temperature ... T$_S$) and 103 (GN$_2$ temperature at the level of the cutting edge ... T$_G$), with a program knob 105 (alternatively: with a series of push buttons or contact sensors 105'), the adjustment range of which corresponds in each case to a working condition of the tank system which it is thus possible easily and accurately to preselect. Apart from the temperature displays for T$_K$, T$_S$ and T$_G$, which can, for instance, be digital display elements 100, 102 and 104, it is possible to provide in this system push buttons 106/107/108 for rapid cooling (RC ... rapid cooling), for rapid heating (RH ....rapid heating) and for heating up the entire chamber upon conclusion of the cryo operation (FH . . . final heating), the logic of which override the programs of 105 and setting positions 99/101/103, so that, for example, all the other settings can be left at the preselection positions needed for the particular operations involved, when the work is started or interrupted. As an alternative to manual control according to FIG. 20, it is possible according to a further development of the invention. As shown in the circuit diagram of FIG. 21, to provide for control via a microprocessor 109 in which the signals of adjusting elements 99'/101'/103', upon preselection of the temperatures $T_K$, $T_S$ and $T_G$, according to the relevant signals from the measuring diodes 50' to 54' and 59 (signal and control line 110) and sensors 65/66/70 (signal line 111) to be automatically converted into control of the heating elements 63/64/69 (control line 112) and 82/82' (control line 113) in such a way that.. .the situation preselected at the elements 99'/101'/103' are brought about as quickly as possible while safeguarding freedom of the chamber from frost. A display 115, while taking into account an acceptable maximum deviation from the preselected values, indicates readiness for working, while displays 114 and 116 signal the fact that the temperature is still rising (signal 116) or falling (signal 114), so that the user must therefore wait until a state of equilibrium is achieved. By a further display 117 having a visual and/or acoustic signal (for example, intermittent flashing and/or beeping), the user can be made aware of the fact that he has preselected a combination of values (e.g. knife temperature $-180°$ C., object temperature $-180°$ C., chamber gas temperature $+5°$ C.) which cannot be feasible. Any display which goes beyond the display of desired and actual values (99'/101'/103' or 100/102/104) can be dispensed with in this system which is the simplest to operate.

Naturally, the invention is not restricted to the embodiment shown in FIGS. 7 to 21. For instance, the inserted tanks 72a/72' may also be combined with other phase separator systems, for example a phase separator tube 45 according to the state of the art, so long as only the $LN_2$ consumption of the system is to be reduced in the temperature range $>-120°$ C. and if the failure of individual microsections at the onset of topping-up with $LN_2$ is not any great problem. Conversely, the separator tank 74 according to the invention can advantageously be used together with the narrow gauge separator tube 73 also in the case of cooling chambers which do not have inserted tanks in the $LN_2$ containers and particularly if one is mainly interested in failure of microsections during the onset of topping-up with $LN_2$. Likewise, the chamber set-up (FIG. 18) according to the invention, in which the cooling chamber is mounted on the microtome base and where only the knife holder is rigidly connected to the cross slide, may also be favourably used in the case of cooling chambers which do not have inserted tanks and which do not have facility for topping-up with $LN_2$ via a separator tank and narrow gauge separator tube. Such a chamber assembly can, for instance, also be combined with a repository surface (FIG. 17) which is coupled to the connecting tube 71, 71' or 71a.

The means according to the invention for monitoring and controlling the operating conditions, according to FIGS. 19 to 21, can be achieved by various means adapted in each case to the selected embodiment of cooling arrangement. This is particularly applicable to the choice of displays and switching elements and the electronics connected to these elements.

We claim:

1. A cooling chamber assembly for attachment to a microtome or ultramicrotome for use in producing thin sections from an object to be used in microscopic investigations, said assembly comprising:

an open-topped cutting chamber, adapted to receive support for an object and for a cutting knife, and defined and bounded laterally and at the bottom by metal walls including first and second opposite, spaced side walls;

first and second tanks positioned on respective opposite sides of said cutting chamber and in communication with each other through connecting means, said tanks being outwardly thermally insulated and forming a tank system;

first and second upwardly open additional tanks inserted and positioned within the interior of said first and second tanks, respectively, and forming part of said tank system, said first and second additional tanks having bottoms spaced above bottoms of said first and second tanks, respectively, and said first and second additional tanks being in communication with each other through communicating means;

separator system means for supplying liquid nitrogen to said tank system by supplying the liquid nitrogen into at least one of said first and second additional tanks, whereby said liquid nitrogen cools said tank system and thereby said cutting chamber as a function of the amount of liquid nitrogen obtained therein, and whereby part of said liquid nitrogen boils off into gaseous nitrogen as a function of the temperature thereof, said separator system means including means for insulating and leading off from said tank system gaseous nitrogen formed during initial supply of liquid nitrogen to said tank system and during subsequent topping-off supply of liquid nitrogen to said tank system;

said first and second tanks having extending downwardly from upper portions thereof toward a bottom portion of said cutting chamber respective first and second baffle means for directing gaseous nitrogen in said first and second tanks to said bottom portion of said cutting chamber, such that the thus directed gaseous nitrogen then traverses said cutting chamber upwardly from said bottom portion thereof and escapes through the open top thereof, thereby cooling said cutting chamber;

at least one of said first and second additional tanks having a wall having a minimum height $H_1$ less than a minimum height $H_2$ of said first and second opposite side walls of said cutting chamber, whereby liquid nitrogen supplied by said separator system means sequentially fills, dependent on the quantity of liquid nitrogen supplied, first said additional tanks, then overflows said wall having said height $H_1$ into said tanks, and then overflows said opposite side walls having said height $H_2$ into said cutting chamber; and heating means, within said cutting chamber, for heating gaseous nitrogen therein, said heating means comprising a heating plate fixed solely to said baffle means without any direct surface contact with any walls of said cutting chamber.

2. An assembly as claimed in claim 1, further comprising sensor means for detecting the level of liquid nitrogen within said additional tanks and operatively connected to said separator systems means for regulating the supply of liquid nitrogen to said tank system.

3. An assembly as claimed in claim 1, wherein said communicating means comprises a tube connecting lower portions of said first and second additional tanks.

4. An assembly as claimed in claim 1, wherein each said additional tank has the interior thereof divided by a respective substantially vertical partition into an outer chamber spaced from said cutting chamber and an inner chamber adjacent said cutting chamber, said communicating means connects said outer chambers, said separator system means supplied the liquid nitrogen into said outer chamber of said at least one of said additional tanks, and each said partition has a minimum height $H_0$ less than said height $H_1$.

5. An assembly as claimed in claim 4, wherein said communicating means comprises a tube connecting lower portions of said outer chambers.

6. An assembly as claimed in claim 4, further comprising heating elements in each of said outer compartments.

7. An assembly as claimed in claim 1, wherein said first and second additional tanks have mutually facing side walls formed by said first and second opposite side walls, respectively, of said cutting chamber.

8. An assembly as claimed in claim 1, wherein each of said additional tanks are mounted within said respective tanks without contact with or attachment to any walls of said cutting chamber.

9. An assembly as claimed in claim 8, wherein outer walls of each of said additional tanks are covered with thermal insulating material.

10. An assembly as claimed in claim 1, wherein said separator system means comprises a closed separated tank within said tank system and separate from said first and second tanks and from said first and second additional tanks, means for supplying liquid nitrogen into said separator tank, means for withdrawing gaseous nitrogen from said separator tank, and a substantially horizontal separator tube extending from said separator tank into said at least one of said first and second additional tanks at a level to be substantially constantly filled with liquid nitrogen.

11. An assembly as claimed in claim 10, wherein said separator tube has a diameter of no more than 4 mm and a length of at least 80 mm.

12. An assembly as claimed in claim 10, wherein said separator tube is rectilinear, and further comprising an additional separator tube having an angled configuration including a substantially vertical portion within said separator tank and having an open inlet end at a height $H_x$ above said height $H_1$ and a substantially horizontal portion extending from said separator tank into said at least one of said first and second additional tanks, parallel to said rectilinear separator tube at a level to be substantially constantly filled with liquid nitrogen.

13. An assembly as claimed in claim 12, wherein the diameter of said additional separator tube is at least equal to the diameter of said rectilinear separator tube.

14. An assembly as claimed in claim 12, further comprising sensor means for detecting the level of liquid nitrogen in said separator tank and for controlling the operation of said supplying means as a function of such detection.

15. An assembly as claimed in claim 14, further comprising a partition within said separator tank at a position to form a splash guard between said sensor means and an inlet of liquid nitrogen into said separator tank.

16. An assembly as claimed in claim 1, further comprising a readily heat-conductive metal intermediate member connected to said connecting means within said cutting chamber, and a readily heat-conductive metal plate connected to said intermediate member and extending therefrom over and covering said heating means, said metal plate being spaced from said heating means by a predetermined distance and being free of direct contact therewith.

17. An assembly as claimed in claim 16, wherein said metal plate is thermally connected to said connecting means via said intermediate member, and said metal plate is thermally insulated form an upper surface of said heating means by thermal insulation.

18. An assembly as claimed in claim 1, further comprising outer metal walls enclosing said cutting chamber and said tank system laterally thereof, means for rigidly connecting said outer metal walls to a base of the microtome or ultramicrotome, a knife support within said cutting chamber, a slide beneath a bottom wall of said cutting chamber, assembly element means for rigidly connecting said slide to said knife support, said assembly element means extending through an opening in a bottom wall of said cutting chamber, and means for sealing said opening and for preventing heating of said cutting chamber through said opening.

19. An assembly as claimed in claim 18, wherein said sealing means comprises a readily heat-conductive metal plate slidingly contacting said bottom wall of said cutting chamber, a resilient heat insulating insert connected to said assembly element means and to said metal plate, and means for urging said metal plate into tight and sealing contact with said bottom wall.

20. An assembly as claimed in claim 19, wherein abutting surfaces of said metal plate and bottom wall are finished to enable sliding therebetween with substantially no friction and to prevent passage therebetween of gaseous nitrogen.

21. An assembly as claimed in claim 19, further comprising means for, upon disconnection of said outer metal walls from the base of the microtome or ultramicrotome, maintaining said metal plate in said tight and sealing contact with said bottom wall.

22. An assembly as claimed in claim 21, wherein said maintaining means comprises at least one support fixed to said bottom wall.

23. An assembly as claimed in claim 19, wherein said sealing means further comprises thermal insulating foam panels positioned above and below said opening in said bottom wall.

24. An assembly as claimed in claim 23, further comprising assembly sleeves connected to said assembly element means and extending upwardly therefrom through said opening into said cutting chamber, said assembly sleeves passing sealingly through said foam panels.

25. An assembly as claimed in claim 1, further comprising means for displaying preselected and/or attained filling conditions of said tank system.

26. An assembly as claimed in claim 25, further comprising means, operatively associated with said displaying means, for adjusting the filling conditions within said tank system as a function of temperatures detected within said cutting chamber.

27. An assembly as claimed in claim 26, further comprising means for detecting a knife temperature, an object temperature and a gas temperature within said cutting chamber, and said adjusting means comprises a microprocessor operable in response to said temperature detector means for controlling operation of said separator system means.

28. An assembly as claimed in claim 27, wherein said microprocessor is operable to determine and indicate when attained filling conditions and/or temperatures are unsuitable for a preselected operation within said cutting chamber.

* * * * *